United States Patent [19]

Petkovich et al.

[11] Patent Number: 6,063,606
[45] Date of Patent: May 16, 2000

[54] RETINOID METABOLIZING PROTEIN

[76] Inventors: P. Martin Petkovich, 875 Everitt Ave., Kingston, Ontario K7M 4R1; Jay A. White, 913 Purcell Crescent, Kingston, Ontario K7P 1C1; Barbara R. Beckett, 112 Westmorland Rd., Kingston, Ontario K7M 1J7; Glenville Jones, 66 Inverness Crescent, Kingston, Ontario K7M 6N7, all of Canada

[21] Appl. No.: 08/724,466

[22] Filed: Oct. 1, 1996

Related U.S. Application Data

[63] Continuation-in-part of application No. 08/667,546, Jun. 21, 1996, abandoned.

[51] Int. Cl.$^7$ .............................. C12N 9/02; C12N 1/20; C12N 15/00; C07M 21/04
[52] U.S. Cl. ................... 435/189; 435/252.3; 435/320.1; 536/23.2; 536/24.1
[58] Field of Search ............................... 435/189, 252.3, 435/320.1; 536/23.2, 24.31, 24.1

[56] References Cited

U.S. PATENT DOCUMENTS 5,330,900  7/1994  Bronstein et al. ........................... 435/6

FOREIGN PATENT DOCUMENTS

| 0 721 984 A1 | 7/1996 | European Pat. Off. . |
| WO 92 16658 | 10/1992 | WIPO . |
| WO 93 22331 | 11/1993 | WIPO . |
| WO 96 23080 | 8/1996 | WIPO . |

OTHER PUBLICATIONS

Raner, G.M. et al., "Metabolism of all–trans, 9–cis, and 13–cis isomers of retinal by purified isozymes of microsomal cytochrome P450 and mechanism–based inhibition of retinoid oxidation by citral", *Mol. Pharmacol.* 49: 515–522 (1996).

Leo, M.A. et al., "Retinoic acid metabolism by a system reconstituted with cytochrome P–450", *Arch. Biochem. Biophys.* 234: 305–312 (1984).

Martini, R. et al., "Participation of P450 3A enzymes in rat hepatic microsomal retinoic acid 4–hydroxylation", *Arch. Biochem. Biophys.* 303: 57–66 (1993).

Marikar, Y. et al., "Regulation, properties, and solubilization of a unique cytochrome P–450 that specifically metabolizes all–trans retinoic acid to less active 4–hydroxy retinoic acid in human keratinocyte HACAT cells", Abstract, *J. Invest. Dermatol.* 106(4): 807 (1996).

White, J.A., et al., "Identification of the retinoic acid–inducible all–trans–retinoic acid 4–hydroxylase", *J. Biol. Chem.* 271: 29922–29927 (1996).

Tomita, S., et al., "Characteristic properties of a retinoic acid synthetic cytochrome P–450 purified from liver microsomes of 3–methylcholanthrene–induced rats", *Biochim. Biophys. Acta* 1290: 273–281 (1996).

Han, I.S., and Choi, J.–H., "Highly specific cytochrome P450–like enzymes for all–trans–retinoic acid in T47D human breast cancer cells", *J. Clin. Endocr. Metab.* 81: 2069–2075 (1996).

Castonguay, A., Overby, L., Nettesheim, P., Clark, G.C., and Philpot, R.M., "Expression of xenobiotic–metabolizing enzymes in cultured rat tracheal epithelial cells", *Environ. Health Perspect.* 103: 254–258 (1995).

Leo, M.A., Lasker, J.M., Raucy, J.L., Kim, C.–I., Black, M. and Lieber, C.S., "Metabolism of retinol and retinoic acid by human liver cytochrome P450llC8", *Arch. Biochem. Biophys.* 269: 305–312 (1989).

Windhorst, D.B., "The use of isotretinoin in disorders of keratinization", *J. Am. Acad. Dermatol.* 6: 708–709 (1982).

Zierold, C., Darwish, H.M., and DeLuca, H.F., "Two vitamin D response elements function in the rat 1,25–dihydroxyvitamin D 24–hydroxylase promoter", *J. Biol. Chem.*, 270: 1675–1678 (1995).

Heng, H.H.Q., and Tsui, L.–C., "Modes of DAPI banding and simultaneous in situ hybridization", *Chromosoma*, 102: 325–332 (1993).

Jones, B.B., Ohno, C.K., Allenby, G., Boffa, M.B., Levin, A.A., Grippo, J.F., and Petkovich, M., "New retinoid X receptor subtypes in zebra fish (*Danio rerio*) differentially modulate transcription and do not bind 9–cis retinoic acid", *Mol. Cell. Biol*, 15: 5226–5234 (1995).

Lammer, E.J., Chen, D.T., Hoar, R.M., Agnish, N.D., Benke, P.J., Braun, J.T., Curry, C.J., Fernhoff, P.M., Grix, A.W., Lott, I.T., Richard, J.M., and Sun, S.C., "Retinoic acid embryopathy", *N. Engl. J. Med.*, 313: 837–841 (1985).

Liang, P., and Pardee, A.B., "Differential display of eukaryotic messenger RNA by means of the polymerase chain reaction", *Science*, 257: 967–971 (1992).

Lichter, P., Tang, C.–J. C., Call, K., Hermanson, G., Evans, G.A., Housman, D., and Ward, D.C., "High–resolution mapping of human chromosome 11 by in situ hybridization with cosmid clones", *Science*, 247: 64–69 (1990).

Maden, M., and Holder, N., "Retinoic acid and development of the central nervous system", *BioEssays*, 14: 431–438 (1992).

Makin, G., Lohnes, D., Byford, V., Ray, R., and Jones, G., "Target cell metabolism of 1,25–dihydroxyvitamin $D_3$ to calcitroic acid", *Biochem. J.*, 262: 173–180 (1989).

Mangelsdorf, D.J., and Evans, R.M., "The RXR heterodimers and orphan receptors", *Cell* 83: 841–850 (1995).

Monia, B.P., Johnston, J.F., Geiger, T., Muller, M., and Fabbro, D., "Antitumor activity of a phosphorothioate antisense oligodeoxynucleotide targeted against C–raf kinase", *Nature Med.*, 2: 668–675 (1996).

Morriss–Kay, G., "Retinoic acid and craniofacial development: molecules and morphogenesis", *BioEssays*, 15: 9–15 (1993).

(List continued on next page.)

*Primary Examiner*—Robert A. Wax
*Assistant Examiner*—Elizabeth Slobodyansky

[57] ABSTRACT

Amino acid sequences and corresponding nucelic acid sequence of retinoid metabolizing protein found in zebrafish and human are described.

32 Claims, 22 Drawing Sheets

(1 of 22 Drawing Sheet(s) Filed in Color)

OTHER PUBLICATIONS

Muindi, J.R.F., Frankel, S.R., Huselton, C., DeGrazia, F., Garland, W.A., Young, C.W., and Warrell, Jr., R.P., "Clinical pharmacology of oral all–trans retinoic acid in patients with acute promyelocytic leukemia", *Cancer Res.*, 52: 2138–2142 (1992).

Muindi, J.R.F., Young, C.W., and Warrell, Jr., R.P., "Clinical pharmacology of all–trans retinoic acid", *Leukemia*, 8: 1807–1812 (1994).

Napoli, J.L., and Race, K.R., "The biosynthesis of retinoic acid from retinol by rat tissues in vitro", *Arch. Biochem. Biophys.*, 255: 95–101 (1987).

Nelson, D.R., Kamataki, T., Waxman, D.J., Guengerich, F.P., Estabrook, R.W., Feyereisen, R., Gonzalez, F.J., Coon, M.J., Gunsalus, I.C., Gotoh, O., Okuda, K., and Nebert, D.W., "The P450 superfamily: update on new sequences, gene mapping, accession numbers, early trivial names of enzymes, and nomenclature", *DNA and Cell Biol.*, 12: 1–51 (1993).

Ohyama, Y., Ozono, K., Uchida, M., Shinki, T., Kato, S., Suda, T., Yamamoto, O., Noshiro, M., and Kato, Y., "Identification of a vitamin D–responsive element in the 5'–flanking region of the rat 25–hydroxyvitamin $D_3$ 24–hydroxylase gene", *J. Biol. Chem.*, 269: 10545–10550 (1994).

Pijnappel, W.W.M., Hendriks, H.F.J., Folkers, G.E., van den Brink, C.E., Dekker, E.J., Edelenbosch, C., van der Saag, P.T., and Durston, A.J., "The retinoid ligand 4–oxo–retinoic acid is a highly active modulator of positional specification", *Nature*, 366: 340–344 (1993).

Reddy, A.P., Chen, J.–Y., Zacharewski, T., Gronemeyer, H., Voorhees, J.J., and Fisher, G.J., "Characterization and purification of human retinoic acid receptor–γ1 overexpressed in the baculovirus–insect cell system", *Biochem J.*, 287: 833–840 (1992).

Thaller, C., and Eichele, G., "Isolation of 3,4–didehydroretinoic acid, a novel morphogenetic signal in the chick wing bud", *Nature*, 345: 815–819 (1990).

White, J.A., Boffa, M.B., Jones, B., and Petkovich, M., "A zebrafish retinoic acid receptor expressed in the regenerating caudal fin", *Development*,120: 1861–1872 (1994).

Roberts, A.B., Frolik, C.A., Nichols, M.D., and Sporn, M.B. "Retinoid–dependent induction of the in vivo and in vitro metabolism of retinoic acid in tissues of the vitamin A–deficient hamster", *J. Biol. Chem.*, 254: 6303–6309 (1979).

Takatsuka, J., Takahashi, N., and De Luca, L.M., "Retinoic acid metabolism and inhibition of cell proliferation: an unexpected liaison", *Cancer Res.*, 56: 675–678 (1996).

van Wauwe, J.P., Ceone, M.–C., Goossens, J., van Nijen, G., Cools, W., and Lauwers, W., "Ketoconazole inhibits the in vitro and in vivo metabolism of all–trans–retinoic acid", *J. Pharm. Exp. Ther.* 245: 718–722 (1988).

van Wauwe, J.P., Coene, M.–C., Goossens, J., Cools, W., and Monbaliu, J., "Effects of cytochrome P–450 inhibitors on the in vivo metabolism of all–trans–retinoic acid in rats", *J. Pharm. Exp. Ther.* 252: 365–369 (1990).

van Wauwe, J.P., van Nyen, G., Ceone, M.–C., Stoppie, P., Cools, W., Goossens, J., Borghgraef, P., and Janssen, P.A.J., "Liarozole, an inhibitor of retinoic acid metabolism, exerts retinoid–mimetic effects in vivo", *J. Pharm. Exp. Ther.* 261: 773–779 (1992).

Williams, J.B., and Napoli, J.L., "Inhibition of retinoic acid metabolism by imidazole antimycotics in F9 embryonal carcinoma cells", *Biochem. Pharm.* 36: 1386–1388 (1987).

Wouters, W., van Dun, J., Dillen, A., Coene, M.–C., Cools, W., and De Coster, R., "Effects of liarozole, a new antitumoral compound, on retinoic acid–induced inhibition of cell growth and on retinoic acid metabolism in MCF–7 human breast cancer cells", *Cancer Res.* 52: 2841–2846 (1992).

Achkar, C.C., Derguini, F., Blumberg, B., Langston, A., Levin, A.A., Speck, J., Evans, R.M., Bolado, Jr., J., Nakanishi, K., Buck, J., and Gudas, L.J., "4–Oxoretinol, a new natural ligand and transactivator of the retinoic acid receptors", *Proc. Natl. Acad. Sci. USA*, 93: 4879–4884 (1996).

Akimenko, M.–A., and Ekker, M., "Anterior duplication of the *Sonic hedgehog* expression pattern in the pectoral fin buds of zebrafish treated with retinoic acid", *Dev. Biol.*, 170: 243–247 (1995).

Akimenko, M.–A., Johnson, S.L., Westerfield, M., and Ekker, M., "Differential induction of four msx homeobox genes during fin development and regeneration in zebrafish", *Development*, 121: 347–357 (1995).

Akiyoshi–Shibata, M., Sakaki, T., Ohyama, Y., Noshiro, M., Okuda, K., and Yabusaki, Y., "Further oxidization of hydroxycalcidiol by calcidiol 24–hydroxylase. A study with the mature enzyme expressed in *Escherichia coli*", *Eur. J. Biochem.*, 224: 335–343 (1994).

Blumberg, B., Bolado, Jr., J., Derguini, F., Craig, A.G., Moreno, T.A., Chakravarti, D., Heyman, R.A., Buck, J., and Evans, R.M., Novel retinoic acid receptor ligands in *Xenopus embryos, Proc. Natl. Acad. Sci. USA*, 93: 4873–4878 (1996).

Boyle, A.L., Feltquite, D.M., Dracopoli, N.C., Housman, D.E., and Ward, D.C., "Rapid physical mapping of cloned DNA on banded mouse chromosomes by fluorescence in situ hybridization", *Genomics* 12: 106–115 (1992).

Chambon, P., "The molecular and genetic dissection of the retinoid signaling pathway", *Recent Progress in Hormone Research*, 50: 317–332 (1995).

Chen, K.–S., and DeLuca, H.F., "Cloning of the human 1 α,25–dihydroxyvitamin D–3 24–hydroxylase gene promoter and identification of two vitamin D–responsive elements", *Biochem. Biophys. Acta*, 1263: 1–9 (1995).

Costardis, P., Horton, C., Zeitlinger, J., Holder, N., and Maden, M., "Endogenous retinoids in the zebrafish embryo and adult", *Dev. Dynamics*, 205: 41–51 (1996).

Creech Kraft, J., Schuh, T., Juchau, M.R., and Kimelman, D., "Temporal disribution, localization and metabolism of all–trans–retinol, didehydroretinol and all–trans–retinal during Xenopus development", *Biochem J.*, 301: 111–119 (1994).

Fiorella, P.D., Guiguère, V., and Napoli, J.L., "Expression of cellular retinoic acid–binding protein (Type II) in *Escherichia coli*", *J. Biol. Chem.*, 268: 21545–21552 (1993).

Green, S., Issemann, I., and Sheer, E., "A versatile in vivo and in vitro eukaryotic expression sector for protein engineering", *Nucl. Acids Res.*, 16: 369 (1988).

Guengerich, F.P., "Reactions and significance of cytochrome P–450 enzymes", *J. Biol. Chem.*, 266: 10019–10022 (1991).

Adamson, P.C., Boylan, J.F., Balis, F.M., Murphy, R.F., Godwin, K.A., Gudas, L.J., and Poplack. D.G., "Time course of induction of metabolism of all–trans–retinoic acid and the up–regulation of cellular retinoic acid–binding protein", *Cancer Res.*, 53: 472–476 (1993).

Boylan, J.F., Lufkin, T., Achkar, C.C., Taneja, R., Chambon, P, and Gudas, L.J., "Targeted disruption of retinoic acid receptor α (RARα) and RARγ results in receptor-specific alterations in retinoic acid-mediated differentiation and retinoic acid metabolism", *Mol. Cell. Biol.*, 15: 843–851 (1995).

Denison, M.S., and Whitlock, Jr., J.P., "Xenobiotic-inducible transcription of cytochrome P450 genes", *J. Biol. Chem.*, 270: 18175–18178 (1995).

Duell, E.A., Åström, A., Griffiths, C.E.M., Chambon, P., and Voorhees, J.J., "Human skin levels of retinoic acid and cytochrome P-450-derived 4-hydroxyretinoic acid after topical application of retinoic acid in vivo compared to concentrations required to stimulate retinoic acid receptor-mediated transcription in vitro", *J. Clin. Invest.*, 90: 1269–1274 (1992).

Duell, E.A., Åström, A., Kang. S., Griffiths, C.E.M., and Voorhees, J.J., "All-trans, 9-cis and 13-cis retinoic acid each induce a cytochrome P450 4-retinoic acid hydroxylase which causes all-trans but not 9-cis or 13-cis retinoic acid to self-metabolize", *SID Abstracts*, 102: 641 (1994).

Frolik, C.A., Roberts, A.B., Tavela, T.E., Roller, P.P., Newton, D.L., and Sporn, M.B., "Isolation and identification of 4-hydroxy- and 4-oxoretinoic acid. In vitro metabolites of all-trans-retinoic acid in hamster trachea and liver", *Biochemistry*, 18: 2092–2097 (1979).

Muindi, J.R.F., Young, C.W., and Warrell, Jr., R.P., "Clinical pharmacology of all-trans retinoic acid", *Leukemia*, 8: S16–S21 (1994).

Roberts, A.B., Nichols, M.D., Newton, D.L., and Sporn, M.B., "In vitro metabolism of retinoic acid in hamster intestine and liver", *J. Biol. Chem.*, 254: 6296–6302 (1979).

Murtha et al. (1991) Proc. Natl. Acad. Sci. USA 88, 10711–10715.

Ogura et al. (Jan. 1995) Proc. Natl. Acad. Sci. USA 92, 387–391.

Hillier et al. (May 1995) accession R51129, EST–STS, EST–STS–TWO databases.

Promega, 1992–1993 Catalog, p. 138.

George et al. (1988) Macromolecular Sequencing and Synthesis, Selected Methods and Applications, pp. 127–149. Alan R. Liss, Inc.

Hillier et al. (Apr. 1995) Accession R22211, EST–STS, EST–STS–TWO databases.

```
MetGlyLeuTyrThrLeuMetValThrPhe   10
LeuCysThrIleValLeuProValLeuLeu   20
PheLeuAlaAlaValLysLeuTrpGluMet   30
LeuMetIleArgArgValAspProAsnCys   40
ArgSerProLeuProProGlyThrMetGly   50
LeuProPheIleGlyGluThrLeuGlnLeu   60
IleLeuGlnArgArgLysPheLeuArgMet   70
LysArgGlnLysTyrGlyCysIleTyrLys   80
ThrHisLeuPheGlyAsnProThrValArg   90
ValMetGlyAlaAspAsnValArgGlnIle  100
LeuLeuGlyGluHisLysLeuValSerVal  110
GlnTrpProAlaSerValArgThrIleLeu  120
GlySerAspThrLeuSerAsnValHisGly  130
ValGlnHisLysAsnLysLysLysAlaIle  140
MetArgAlaPheSerArgAspAlaLeuGlu  150
HisTyrIleProValIleGlnGlnGluVal  160
LysSerAlaIleGlnGluTrpLeuGlnLys  170
AspSerCysValLeuValTyrProGluMet  180
LysLysLeuMetPheArgIleAlaMetArg  190
IleLeuLeuGlyPheGluProGluGlnIle  200
LysThrAspGluGlnGluLeuValGluAla  210
PheGluGluMetIleLysAsnLeuPheSer  220
LeuProIleAspValProPheSerGlyLeu  230
TyrArgGlyLeuArgAlaArgAsnPheIle  240
HisSerLysIleGluGluAsnIleArgLys  250
LysIleGlnAspAspAspAsnGluAsnGlu  260
GlnLysTyrLysAspAlaLeuGlnLeuLeu  270
```

FIG. 2C(i)

```
IleGluAsnSerArgArgSerAspGluPro      280
PheSerLeuGlnAlaMetLysGluAlaAla      290
ThrGluLeuLeuPheGlyGlyHisGluThr      300
ThrAlaSerThrAlaThrSerLeuValMet      310
PheLeuGlyLeuAsnThrGluValValGln      320
LysValArgGluGluValGlnGluLysVal      330
GluMetGlyMetTyrThrProGlyLysGly      340
LeuSerMetGluLeuLeuAspGlnLeuLys      350
TyrThrGlyCysValIleLysGluThrLeu      360
ArgIleAsnProProValProGlyGlyPhe      370
ArgValAlaLeuLysThrPheGluLeuAsn      380
GlyTyrGlnIleProLysGlyTrpAsnVal      390
IleTyrSerIleCysAspThrHisAspVal      400
AlaAspValPheProAsnLysGluGluPhe      410
GlnProGluArgPheMetSerLysGlyLeu      420
GluAspGlySerArgPheAsnTyrIlePro      430
PheGlyGlyGlySerArgMetCysValGly      440
LysGluPheAlaLysValLeuLeuLysIle      450
PheLeuValGluLeuThrGlnHisCysAsn      460
TrpIleLeuSerAsnGlyProProThrMet      470
LysThrGlyProThrIleTyrProValAsp      480
AsnLeuProThrLysPheThrSerTyrVal      490
ArgAsn                              492
```

FIG. 2C(ii)

```
              -8   -4   0    4    8
P450RAI       PFGGGSRMCVGKEFAKVLLK
ATCYTP450     *****P*L*P*Y*L*R*A*S
RATCYP4A1     SA*N*IQMSEM*
RABCYP4A5     SA*N*IQMNE**
CYP4503A12    ***T*P*N*I*MR**IMNM*
hCYTFAOH      S**N*IQMNE**
```

FIG. 2D

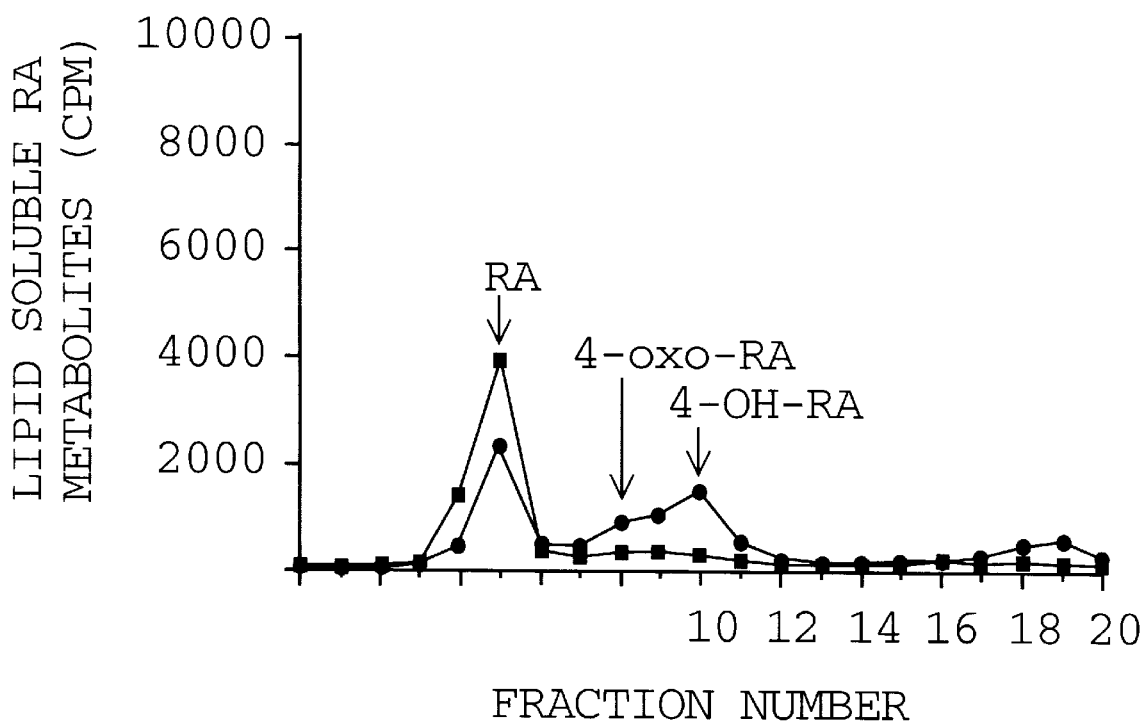
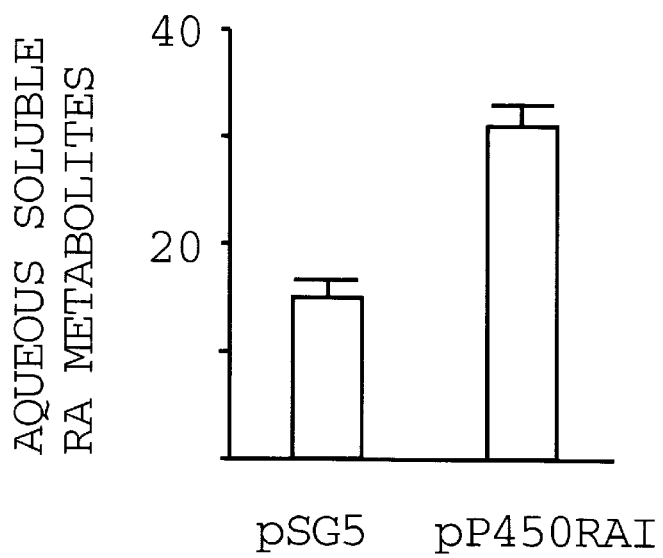
FIG. 4B

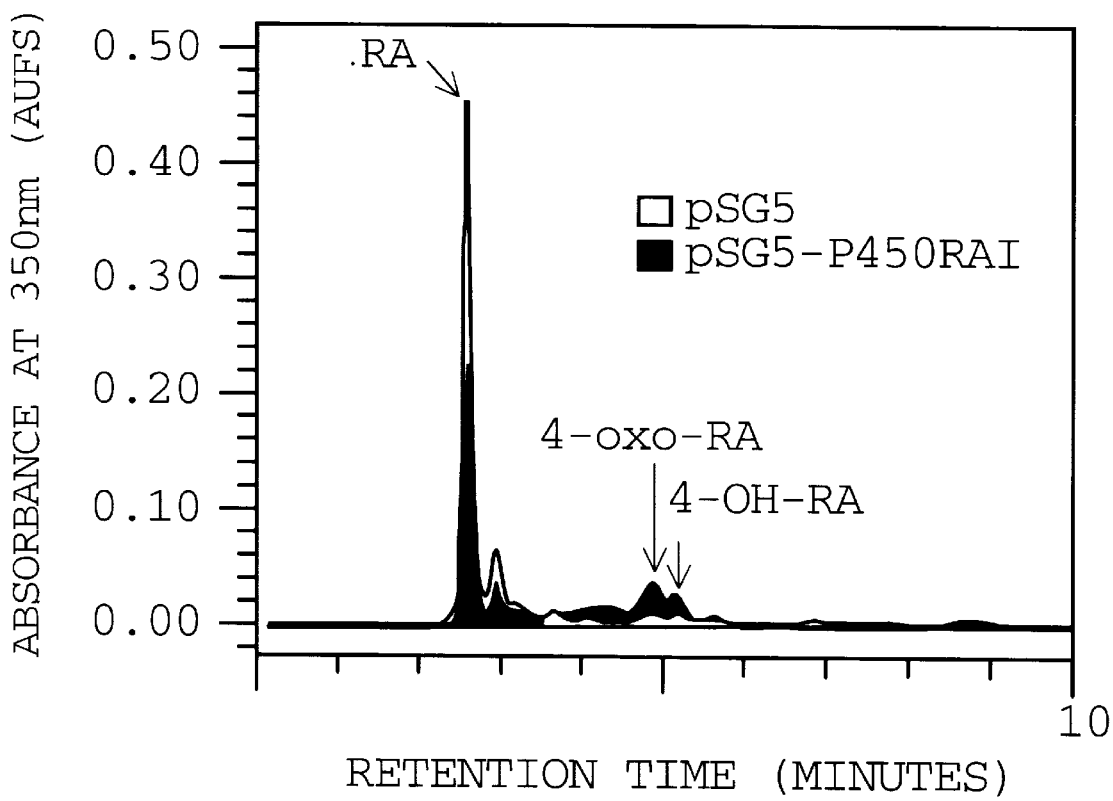
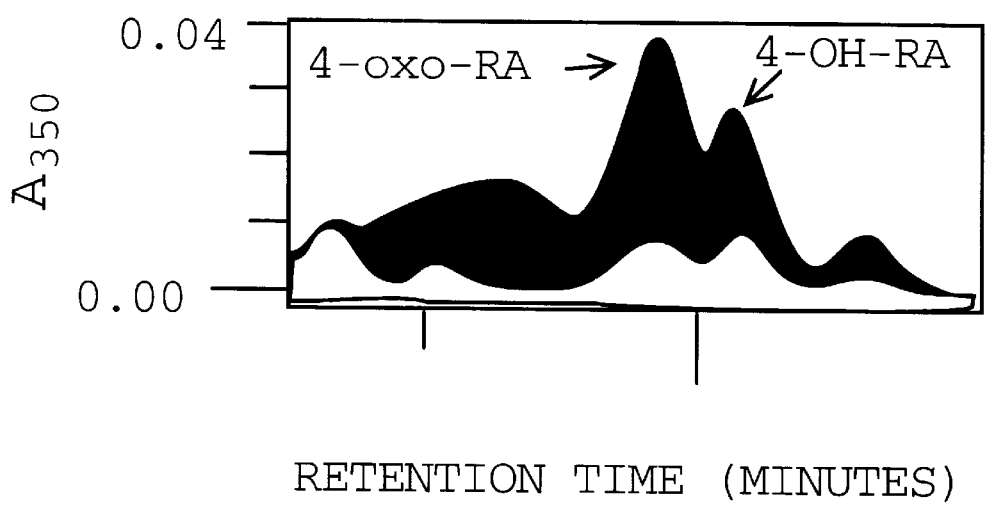
FIG. 4C

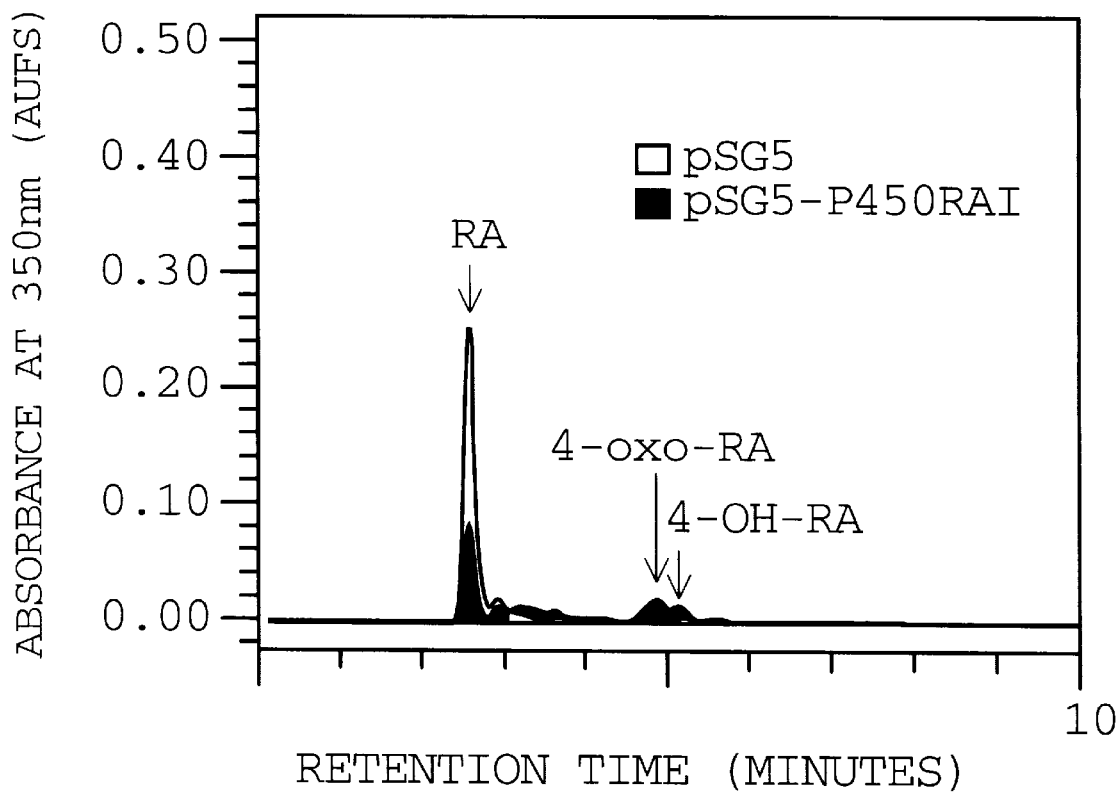
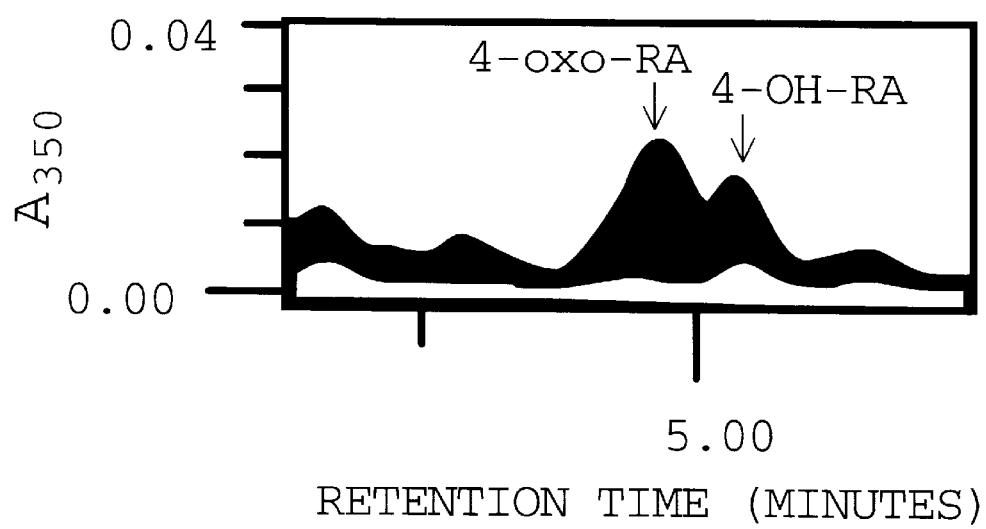
FIG. 4D

```
mP450RAI  MGLPALLASALCTFVLPLLLFLAALKLWDLYCVSSRDRSCALPLPPGTMGFPFFGETLQM   60
hP450RAI  ..............I..............G..............................   60
zP450RAI  ...YT.MVTF...I...V......V...EMLMIRRV.PN.RS.........L..I.....L  60 mP450RAI  VLQRRKFLQMKRRKYGFIYKTHLFGRPTVRVMGADNVRRILLGEHRLVSVHWPASVRTIL    120
hP450RAI  ..........................................DD..............    120
zP450RAI  I......R..Q...C.........N............Q......K....Q.........   120 mP450RAI  GAGCLSNLHDSSHKQRKKVIMQAFSREALQCYVLVIAEEVSSCLEQWLSCGERGLLVYPE    180
hP450RAI  .S...............................R......E...P..T...G.S....    180
zP450RAI  .SDT...V.GVQ..NK..A..R....D..EH.IP..QQ..K.AIQE..Q-KDSCV....   179 mP450RAI  VKRLMFRIAMRILLGCEPGPAGGGEDEQQLVEAFEEMTRNLFSLPIDVPFFSGLYRGVKAR   240
hP450RAI  ...................QL..D.DS.................M...............  240
zP450RAI  M.K.............F..EQI--KT...E.......IK.........LR..........  237 mP450RAI  NLIHARIEENIRAKIRRLQATEPDGGCKDALQLLIEHSWERGERLDMQALKQSSTELLFG   300
hP450RAI  .......Q......CG.R.S.AGQ..................................   300
zP450RAI  .F..SK......K..QDDDNENEQ-KY..........N.RRSD.PFSL..M.EAA....   296
```

FIG. 9A

```
mP450RAI   GHETTASAATSLITYLGLYPHVLQKVREEIKSKGLLCKSNQDNKLDMETLEQLKYIGCVI   360
hP450RAI   ............................................I...............   360
zP450RAI   .....T....VMF...NTE.V......VQE.VEMGMYTPGKG.S..L.D....T......   356 mP450RAI   KETLRLNPPVGGFRVALKTFELNGYQIPKGWNVIYSICDTHDVADIFTNKEEFNPDRFI     420
hP450RAI   ...............................E...........................   420
zP450RAI   ....I..........................................V.P.....Q.E..M 416 mP450RAI   VPHPEDASRFSFIPFGGGLRSCVGKEFAKILLKIFTVELARHCDWQLLNGPPTMKTSPTV    480
hP450RAI   A...........................................................   480
zP450RAI   SKGL..G...NY........S.M.......V.....L..TQ..N.I.S........G..I   476 mP450RAI   YPVDNLPARFTYFQGDI                                               497
hP450RAI   ...........H.H.E.                                               497
zP450RAI   .......TK..SYVRN-                                               492
```

FIG. 9B

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 337 base pairs
      (B) TYPE: nucleic acid
      (C) STRANDEDNESS: single
      (D) TOPOLOGY: linear (xi) SEQUENCE DESCRIPTION: SEQ ID NO:1:

```
TGCCAGTGGA CAATCTCCCT ACCAAATTCA CTAGTTATGT CCAGAAATTA GCCTAAACCG      60

GAGCCTTTGT ACATATGTTT TTATTTTAGA TGAACTGTGA TGTATTGGAT ATTTTCTAAT     120

TTGTTTATAT AAAGCAGATG TGTATATAAG TCTATGCGAA GAAGCGAAAA CGAGGGCACT     180

ACTTTCTCAT GGATCACTGT AATGCTACAG AGTGTCTGTG ATGTATATTT ATAATGTAGT     240

TGTGTCATAT AGCTTTTGTA CTGTATGCAA CTTATTTAAC TCGCTCTTTA TCTCATGGGT     300

TTTATTTAAT AAAACATGTT CTTACAAAAA AAAAAAA                              337
```

(2) INFORMATION FOR SEQ ID NO:2:

(i) SEQUENCE CHARACTERISTICS:
      (A) LENGTH: 492 amino acids
      (B) TYPE: amino acid
      (C) STRANDEDNESS: single
      (D) TOPOLOGY: linear (xi) SEQUENCE DESCRIPTION: SEQ ID NO:2:

```
Met Gly Leu Tyr Thr Leu Met Val Thr Phe Leu Cys Thr Ile Val Leu
1               5                  10                  15

Pro Val Leu Leu Phe Leu Ala Ala Val Lys Leu Trp Glu Met Leu Met
                20                  25                  30

Ile Arg Arg Val Asp Pro Asn Cys Arg Ser Pro Leu Pro Pro Gly Thr
            35                  40                  45

Met Gly Leu Pro Phe Ile Gly Glu Thr Leu Gln Leu Ile Leu Gln Arg
        50                  55                  60

Arg Lys Phe Leu Arg Met Lys Arg Gln Lys Tyr Gly Cys Ile Tyr Lys
65                  70                  75                  80

Thr His Leu Phe Gly Asn Pro Thr Val Arg Val Met Gly Ala Asp Asn
                85                  90                  95

Val Arg Gln Ile Leu Leu Gly Glu His Lys Leu Val Ser Val Gln Trp
```

```
                    100                 105                 110
Pro Ala Ser Val Arg Thr Ile Leu Gly Ser Asp Thr Leu Ser Asn Val
            115                 120                 125
His Gly Val Gln His Lys Asn Lys Lys Ala Ile Met Arg Ala Phe
130                 135                 140
Ser Arg Asp Ala Leu Glu His Tyr Ile Pro Val Ile Gln Gln Glu Val
145                 150                 155                 160
Lys Ser Ala Ile Gln Glu Trp Leu Gln Lys Asp Ser Cys Val Leu Val
                165                 170                 175
Tyr Pro Glu Met Lys Lys Leu Met Phe Arg Ile Ala Met Arg Ile Leu
                180                 185                 190
Leu Gly Phe Glu Pro Glu Gln Ile Lys Thr Asp Glu Gln Glu Leu Val
                195                 200                 205
Glu Ala Phe Glu Glu Met Ile Lys Asn Leu Phe Ser Leu Pro Ile Asp
            210                 215                 220
Val Pro Phe Ser Gly Leu Tyr Arg Gly Leu Arg Ala Arg Asn Phe Ile
225                 230                 235                 240
His Ser Lys Ile Glu Glu Asn Ile Arg Lys Lys Ile Gln Asp Asp Asp
                245                 250                 255
Asn Glu Asn Glu Gln Lys Tyr Lys Asp Ala Leu Gln Leu Leu Ile Glu
            260                 265                 270
Asn Ser Arg Arg Ser Asp Glu Pro Phe Ser Leu Gln Ala Met Lys Glu
            275                 280                 285
Ala Ala Thr Glu Leu Leu Phe Gly Gly His Glu Thr Thr Ala Ser Thr
            290                 295                 300
Ala Thr Ser Leu Val Met Phe Leu Gly Leu Asn Thr Glu Val Val Gln
305                 310                 315                 320
Lys Val Arg Glu Glu Val Gln Glu Lys Val Glu Met Gly Met Tyr Thr
                325                 330                 335
Pro Gly Lys Gly Leu Ser Met Glu Leu Leu Asp Gln Leu Lys Tyr Thr
                340                 345                 350
Gly Cys Val Ile Lys Glu Thr Leu Arg Ile Asn Pro Pro Val Pro Gly
                355                 360                 365
Gly Phe Arg Val Ala Leu Lys Thr Phe Glu Leu Asn Gly Tyr Gln Ile
            370                 375                 380
Pro Lys Gly Trp Asn Val Ile Tyr Ser Ile Cys Asp Thr His Asp Val
385                 390                 395                 400
Ala Asp Val Phe Pro Asn Lys Glu Glu Phe Gln Pro Glu Arg Phe Met
                405                 410                 415
Ser Lys Gly Leu Glu Asp Gly Ser Arg Phe Asn Tyr Ile Pro Phe Gly
                420                 425                 430
Gly Gly Ser Arg Met Cys Val Gly Lys Glu Phe Ala Lys Val Leu Leu
                435                 440                 445
Lys Ile Phe Leu Val Glu Leu Thr Gln His Cys Asn Trp Ile Leu Ser
            450                 455                 460
Asn Gly Pro Pro Thr Met Lys Thr Gly Pro Thr Ile Tyr Pro Val Asp
465                 470                 475                 480
Asn Leu Pro Thr Lys Phe Thr Ser Tyr Val Arg Asn
                485                 490

(2) INFORMATION FOR SEQ ID NO:3:

(i) SEQUENCE CHARACTERISTICS:
        (A) LENGTH: 1850 base pairs
```

(B) TYPE: nucleic acid
(C) STRANDEDNESS: single
(D) TOPOLOGY: linear (xi) SEQUENCE DESCRIPTION: SEQ ID NO:3:

```
TGTCGCCGTT GCTGTCGGTT GCTGTCGGAC GCTGTCTCCT CTCCAGAAGC TTGTTTTTCG        60

TTTTGGCGAT CAGTTGCGCG CTTCAAC ATG GGG CTG TAC ACC CTT ATG GTC ACC       114
                             Met Gly Leu Tyr Thr Leu Met Val Thr
                              1               5

TTT CTC TGC ACC ATC GTG CTA CCC GTT TTA CTC TTT CTC GCC GCG GTG         162
Phe Leu Cys Thr Ile Val Leu Pro Val Leu Leu Phe Leu Ala Ala Val
 10              15                  20                  25

AAG TTG TGG GAG ATG TTA ATG ATC CGA CGA GTC GAT CCG AAC TGC AGA         210
Lys Leu Trp Glu Met Leu Met Ile Arg Arg Val Asp Pro Asn Cys Arg
             30                  35                  40

AGT CCT CTA CCG CCA GGT ACC ATG GGC TTG CCG TTC ATT GGA GAA ACG         258
Ser Pro Leu Pro Pro Gly Thr Met Gly Leu Pro Phe Ile Gly Glu Thr
                 45                  50                  55

CTC CAG CTG ATC CTC CAG AGA AGG AAG TTT CTG CGC ATG AAA CGG CAG         306
Leu Gln Leu Ile Leu Gln Arg Arg Lys Phe Leu Arg Met Lys Arg Gln
             60                  65                  70

AAA TAC GGG TGC ATC TAC AAG ACG CAC CTC TTC GGG AAC CCG ACT GTC         354
Lys Tyr Gly Cys Ile Tyr Lys Thr His Leu Phe Gly Asn Pro Thr Val
 75                  80                  85

AGG GTG ATG GGA GCT GAT AAT GTG AGG CAG ATT CTG CTG GGC GAA CAC         402
Arg Val Met Gly Ala Asp Asn Val Arg Gln Ile Leu Leu Gly Glu His
 90                  95                 100                 105

AAG CTG GTG TCT GTT CAG TGG CCA GCA TCA GTG AGA ACC ATC CTG GGC         450
Lys Leu Val Ser Val Gln Trp Pro Ala Ser Val Arg Thr Ile Leu Gly
                110                 115                 120

TCT GAC ACC CTC TCC AAT GTC CAT GGA GTT CAA CAC AAA AAC AAG AAA         498
Ser Asp Thr Leu Ser Asn Val His Gly Val Gln His Lys Asn Lys Lys
                125                 130                 135

AAG GCC ATT ATG AGG GCG TTC TCT CGA GAT GCT CTG GAG CAC TAC ATT         546
Lys Ala Ile Met Arg Ala Phe Ser Arg Asp Ala Leu Glu His Tyr Ile
                140                 145                 150

CCC GTG ATC CAG CAG GAG GTG AAG AGC GCC ATA CAG GAA TGG CTG CAA         594
Pro Val Ile Gln Gln Glu Val Lys Ser Ala Ile Gln Glu Trp Leu Gln
                155                 160                 165

AAA GAC TCC TGC GTG CTG GTT TAT CCA GAA ATG AAG AAA CTC ATG TTT         642
Lys Asp Ser Cys Val Leu Val Tyr Pro Glu Met Lys Lys Leu Met Phe
170                 175                 180                 185

CGG ATA GCT ATG AGA ATC CTG CTT GGT TTT GAA CCA GAG CAA ATA AAG         690
Arg Ile Ala Met Arg Ile Leu Leu Gly Phe Glu Pro Glu Gln Ile Lys
                190                 195                 200

ACG GAC GAG CAA GAA CTG GTG GAA GCT TTT GAG GAA ATG ATC AAA AAC         738
Thr Asp Glu Gln Glu Leu Val Glu Ala Phe Glu Glu Met Ile Lys Asn
                205                 210                 215

TTG TTC TCC TTG CCA ATC GAC GTT CCT TTC AGT GGT CTG TAC AGG GGT         786
Leu Phe Ser Leu Pro Ile Asp Val Pro Phe Ser Gly Leu Tyr Arg Gly
                220                 225                 230

TTG AGG GCA CGC AAT TTC ATT CAC TCC AAA ATT GAG GAA AAC ATC AGG         834
Leu Arg Ala Arg Asn Phe Ile His Ser Lys Ile Glu Glu Asn Ile Arg
            235                 240                 245

AAG AAA ATT CAA GAT GAC GAC AAT GAA AAC GAA CAG AAA TAC AAA GAC         882
Lys Lys Ile Gln Asp Asp Asp Asn Glu Asn Glu Gln Lys Tyr Lys Asp
250                 255                 260                 265

GCC CTT CAG CTG TTG ATC GAG AAC AGC AGA AGA AGT GAC GAA CCT TTT         930
Ala Leu Gln Leu Leu Ile Glu Asn Ser Arg Arg Ser Asp Glu Pro Phe
                270                 275                 280
```

```
AGT TTG CAG GCG ATG AAA GAA GCA GCT ACA GAG CTT CTA TTT GGA GGT      978
Ser Leu Gln Ala Met Lys Glu Ala Ala Thr Glu Leu Leu Phe Gly Gly
            285                 290                 295

CAT GAA ACC ACC GCC AGC ACT GCA ACC TCA CTT GTC ATG TTT CTG GGT     1026
His Glu Thr Thr Ala Ser Thr Ala Thr Ser Leu Val Met Phe Leu Gly
                300                 305                 310

CTG AAC ACA GAA GTG GTG CAG AAG GTC AGA GAG GAG GTT CAG GAG AAG     1074
Leu Asn Thr Glu Val Val Gln Lys Val Arg Glu Glu Val Gln Glu Lys
        315                 320                 325

GTT GAA ATG GGC ATG TAT ACA CCT GGA AAG GGC TTG AGT ATG GAG CTG     1122
Val Glu Met Gly Met Tyr Thr Pro Gly Lys Gly Leu Ser Met Glu Leu
330                 335                 340                 345

TTG GAC CAG CTG AAG TAC ACT GGA TGT GTG ATT AAA GAG ACT CTT AGA     1170
Leu Asp Gln Leu Lys Tyr Thr Gly Cys Val Ile Lys Glu Thr Leu Arg
                350                 355                 360

ATC AAC CCT CCT GTT CCC GGA GGA TTC AGA GTC GCA CTC AAA ACC TTT     1218
Ile Asn Pro Pro Val Pro Gly Gly Phe Arg Val Ala Leu Lys Thr Phe
                365                 370                 375

GAA TTG AAT GGT TAC CAA ATT CCT AAA GGA TGG AAC GTC ATT TAC AGC     1266
Glu Leu Asn Gly Tyr Gln Ile Pro Lys Gly Trp Asn Val Ile Tyr Ser
        380                 385                 390

ATC TGT GAC ACG CAC GAT GTG GCC GAC GTC TTT CCA AAC AAA GAG GAG     1314
Ile Cys Asp Thr His Asp Val Ala Asp Val Phe Pro Asn Lys Glu Glu
395                 400                 405

TTC CAG CCG GAG AGA TTC ATG AGC AAA GGT CTG GAG GAC GGG TCC AGG     1362
Phe Gln Pro Glu Arg Phe Met Ser Lys Gly Leu Glu Asp Gly Ser Arg
410                 415                 420                 425

TTT AAC TAC ATC CCC TTC GGA GGA GGA TCC AGG ATG TGT GTG GGC AAA     1410
Phe Asn Tyr Ile Pro Phe Gly Gly Gly Ser Arg Met Cys Val Gly Lys
                430                 435                 440

GAG TTC GCC AAA GTG TTA CTC AAG ATC TTT TTA GTT GAG TTA ACG CAG     1458
Glu Phe Ala Lys Val Leu Leu Lys Ile Phe Leu Val Glu Leu Thr Gln
            445                 450                 455

CAT TGC AAT TGG ATT CTC TCA AAC GGA CCC CCG ACA ATG AAA ACA GGC     1506
His Cys Asn Trp Ile Leu Ser Asn Gly Pro Pro Thr Met Lys Thr Gly
                460                 465                 470

CCG ACT ATT TAC CCA GTG GAC AAT CTC CCT ACC AAA TTC ACT AGT TAT     1554
Pro Thr Ile Tyr Pro Val Asp Asn Leu Pro Thr Lys Phe Thr Ser Tyr
475                 480                 485

GTC AGA AAT TAGCCTAACC GGAGCTTTGT ACATATGTTT TTATTTAGA              1603
Val Arg Asn
490

TGAACTGTGA TGTATTGGAT ATTTTCTATT TTGTTTATAT AAAGCAGATG TGTATATAAG   1663

TCTATGCGAG GAAGCGAAAA CGAGGGCACT ACTTTCTCAT GGATCACTGT AATGCTACAG   1723

AGTGTCTGTG ATGTATATTT ATAATGTAGT TGTGTTATAT AGCTTTTGTA CTGTATGCAA   1783

CTTATTTAAC TCGCTCTTTA TCTCATGGGT TTTATTTAAT AAAACATGTT CTTACAAAAA   1843

AAAAAAA                                                             1850

(2) INFORMATION FOR SEQ ID NO:4:

(i) SEQUENCE CHARACTERISTICS:
        (A) LENGTH: 497 amino acids
        (B) TYPE: amino acid
        (C) STRANDEDNESS: single
        (D) TOPOLOGY: linear (xi) SEQUENCE DESCRIPTION: SEQ ID NO:4:

Met Gly Leu Pro Ala Leu Leu Ala Ser Ala Leu Cys Thr Phe Val Leu
```

-continued

```
  1               5                  10                 15
Pro Leu Leu Leu Phe Leu Ala Ala Ile Lys Leu Trp Asp Leu Tyr Cys
                 20                  25                 30

Val Ser Gly Arg Asp Arg Ser Cys Ala Leu Pro Leu Pro Pro Gly Thr
                 35                  40                 45

Met Gly Phe Pro Phe Phe Gly Glu Thr Leu Gln Met Val Leu Gln Arg
     50                  55                  60

Arg Lys Phe Leu Gln Met Lys Arg Lys Tyr Gly Phe Ile Tyr Lys
 65                  70                  75                 80

Thr His Leu Phe Gly Arg Pro Thr Val Arg Val Met Gly Ala Asp Asn
                 85                  90                 95

Val Arg Arg Ile Leu Leu Gly Asp Asp Arg Leu Val Ser Val His Trp
                100                 105                110

Pro Ala Ser Val Arg Thr Ile Leu Gly Ser Gly Cys Leu Ser Asn Leu
                115                 120                125

His Asp Ser Ser His Lys Gln Arg Lys Val Ile Met Arg Ala Phe
                130                 135                140

Ser Arg Glu Ala Leu Glu Cys Tyr Val Pro Val Ile Thr Glu Glu Val
145                 150                 155                160

Gly Ser Ser Leu Glu Gln Trp Leu Ser Cys Gly Glu Arg Gly Leu Leu
                165                 170                175

Val Tyr Pro Glu Val Lys Arg Leu Met Phe Arg Ile Ala Met Arg Ile
                180                 185                190

Leu Leu Gly Cys Glu Pro Gln Leu Ala Gly Asp Gly Asp Ser Glu Gln
                195                 200                205

Gln Leu Val Glu Ala Phe Glu Glu Met Thr Arg Asn Leu Phe Ser Leu
     210                 215                 220

Pro Ile Asp Val Pro Phe Ser Gly Leu Tyr Arg Gly Met Lys Ala Arg
225                 230                 235                240

Asn Leu Ile His Ala Arg Ile Glu Gln Asn Ile Arg Ala Lys Ile Cys
                245                 250                255

Gly Leu Arg Ala Ser Glu Ala Gly Gln Gly Cys Lys Asp Ala Leu Gln
                260                 265                270

Leu Leu Ile Glu His Ser Trp Glu Arg Gly Glu Arg Leu Asp Met Gln
                275                 280                285

Ala Leu Lys Gln Ser Ser Thr Glu Leu Leu Phe Gly Gly His Glu Thr
     290                 295                 300

Thr Ala Ser Ala Ala Thr Ser Leu Ile Thr Tyr Leu Gly Leu Tyr Pro
305                 310                 315                320

His Val Leu Gln Lys Val Arg Glu Glu Leu Lys Ser Lys Gly Leu Leu
                325                 330                335

Cys Lys Ser Asn Gln Asp Asn Lys Leu Asp Met Glu Ile Leu Glu Gln
                340                 345                350

Leu Lys Tyr Ile Gly Cys Val Ile Lys Glu Thr Leu Arg Leu Asn Pro
                355                 360                365

Pro Val Pro Gly Gly Phe Arg Val Ala Leu Lys Thr Phe Glu Leu Asn
     370                 375                 380

Gly Tyr Gln Ile Pro Lys Gly Trp Asn Val Ile Tyr Ser Ile Cys Asp
385                 390                 395                400

Thr His Asp Val Ala Glu Ile Phe Thr Asn Lys Glu Phe Asn Pro
                405                 410                415

Asp Arg Phe Ser Ala Pro His Pro Glu Asp Ala Ser Arg Phe Ser Phe
                420                 425                430
```

```
Ile Pro Phe Gly Gly Leu Arg Ser Cys Val Gly Lys Glu Phe Ala
        435                 440                 445

Lys Ile Leu Leu Lys Ile Phe Thr Val Glu Leu Ala Arg His Cys Asp
450                 455                 460

Trp Gln Leu Leu Asn Gly Pro Pro Thr Met Lys Thr Ser Pro Thr Val
465                 470                 475                 480

Tyr Pro Val Asp Asn Leu Pro Ala Arg Phe Thr His Phe His Gly Glu
                485                 490                 495

Ile
```

(2) INFORMATION FOR SEQ ID NO:5:

(i) SEQUENCE CHARACTERISTICS:
        (A) LENGTH: 1494 base pairs
        (B) TYPE: nucleic acid
        (C) STRANDEDNESS: single
        (D) TOPOLOGY: linear (xi) SEQUENCE DESCRIPTION: SEQ ID NO:5:

```
ATG GGG CTC CCG GCG CTG CTG GCC AGT GCG CTC TGC ACC TTC GTG CTG         48
Met Gly Leu Pro Ala Leu Leu Ala Ser Ala Leu Cys Thr Phe Val Leu
 1               5                  10                  15

CCG CTG CTG CTC TTC CTG GCT GCG ATC AAG CTC TGG GAC CTG TAC TGC         96
Pro Leu Leu Leu Phe Leu Ala Ala Ile Lys Leu Trp Asp Leu Tyr Cys
             20                  25                  30

GTG AGC GGC CGC GAC CGC AGT TGT GCC CTC CCA TTG CCC CCC GGG ACT        144
Val Ser Gly Arg Asp Arg Ser Cys Ala Leu Pro Leu Pro Pro Gly Thr
         35                  40                  45

ATG GGC TTC CCC TTC TTT GGG GAA ACC TTG CAG ATG GTA CTG CAG CGG        192
Met Gly Phe Pro Phe Phe Gly Glu Thr Leu Gln Met Val Leu Gln Arg
 50                  55                  60

AGG AAG TTC CTG CAG ATG AAG CGC AGG AAA TAC GGC TTC ATC TAC AAG        240
Arg Lys Phe Leu Gln Met Lys Arg Arg Lys Tyr Gly Phe Ile Tyr Lys
 65                  70                  75                  80

ACG CAT CTG TTC GGG CGG CCC ACC GTA CGG GTG ATG GGC GCG GAC AAT        288
Thr His Leu Phe Gly Arg Pro Thr Val Arg Val Met Gly Ala Asp Asn
                 85                  90                  95

GTG CGG CGC ATC TTG CTC GGA GAC GAC CGG CTG GTG TCG GTC CAC TGG        336
Val Arg Arg Ile Leu Leu Gly Asp Asp Arg Leu Val Ser Val His Trp
            100                 105                 110

CCA GCG TCG GTG CGC ACC ATT CTG GGA TCT GGC TGC CTC TCT AAC CTG        384
Pro Ala Ser Val Arg Thr Ile Leu Gly Ser Gly Cys Leu Ser Asn Leu
        115                 120                 125

CAC GAC TCC TCG CAC AAG CAG CGC AAG AAG GTG ATT ATG CGG GCC TTC        432
His Asp Ser Ser His Lys Gln Arg Lys Lys Val Ile Met Arg Ala Phe
    130                 135                 140

AGC CGC GAG GCA CTC GAA TGC TAC GTG CCG GTG ATC ACC GAG GAA GTG        480
Ser Arg Glu Ala Leu Glu Cys Tyr Val Pro Val Ile Thr Glu Glu Val
145                 150                 155                 160

GGC AGC AGC CTG GAG CAG TGG CTG AGC TGC GGC GAG CGC GGC CTC CTG        528
Gly Ser Ser Leu Glu Gln Trp Leu Ser Cys Gly Glu Arg Gly Leu Leu
                165                 170                 175

GTC TAC CCC GAG GTG AAG CGC CTC ATG TTC CGA ATC GCC ATG CGC ATC        576
Val Tyr Pro Glu Val Lys Arg Leu Met Phe Arg Ile Ala Met Arg Ile
            180                 185                 190

CTA CTG GGC TGC GAA CCC CAA CTG GCG GGC GAC GGG GAC TCC GAG CAG        624
Leu Leu Gly Cys Glu Pro Gln Leu Ala Gly Asp Gly Asp Ser Glu Gln
        195                 200                 205

CAG CTT GTG GAG GCC TTC GAG GAA ATG ACC CGC AAT CTC TTC TCG CTG        672
```

```
Gln Leu Val Glu Ala Phe Glu Glu Met Thr Arg Asn Leu Phe Ser Leu
        210                 215                 220

CCC ATC GAC GTG CCC TTC AGC GGG CTG TAC CGG GGC ATG AAG GCG CGG        720
Pro Ile Asp Val Pro Phe Ser Gly Leu Tyr Arg Gly Met Lys Ala Arg
225                 230                 235                 240

AAC CTC ATT CAC GCG CGC ATC GAG CAG AAC ATT CGC GCC AAG ATC TGC        768
Asn Leu Ile His Ala Arg Ile Glu Gln Asn Ile Arg Ala Lys Ile Cys
                245                 250                 255

GGG CTG CGG GCA TCC GAG GCG GGC CAG GGC TGC AAA GAC GCG CTG CAG        816
Gly Leu Arg Ala Ser Glu Ala Gly Gln Gly Cys Lys Asp Ala Leu Gln
            260                 265                 270

CTG TTG ATC GAG CAC TCG TGG GAG AGG GGA GAG CGG CTG GAC ATG CAG        864
Leu Leu Ile Glu His Ser Trp Glu Arg Gly Glu Arg Leu Asp Met Gln
        275                 280                 285

GCA CTA AAG CAA TCT TCA ACC GAA CTC CTC TTT GGA GGA CAC GAA ACC        912
Ala Leu Lys Gln Ser Ser Thr Glu Leu Leu Phe Gly Gly His Glu Thr
290                 295                 300

ACG GCC AGT GCA GCC ACA TCT CTG ATC ACT TAC CTG GGG CTC TAC CCA        960
Thr Ala Ser Ala Ala Thr Ser Leu Ile Thr Tyr Leu Gly Leu Tyr Pro
305                 310                 315                 320

CAT GTT CTC CAG AAA GTG CGA GAA GAG CTG AAG AGT AAG GGT TTA CTT       1008
His Val Leu Gln Lys Val Arg Glu Glu Leu Lys Ser Lys Gly Leu Leu
                325                 330                 335

TGC AAG AGC AAT CAA GAC AAC AAG TTG GAC ATG GAA ATT TTG GAA CAA       1056
Cys Lys Ser Asn Gln Asp Asn Lys Leu Asp Met Glu Ile Leu Glu Gln
            340                 345                 350

CTT AAA TAC ATC GGG TGT GTT ATT AAG GAG ACC CTT CGA CTG AAT CCC       1104
Leu Lys Tyr Ile Gly Cys Val Ile Lys Glu Thr Leu Arg Leu Asn Pro
        355                 360                 365

CCA GTT CCA GGA GGG TTT CGG GTT GCT CTG AAG ACT TTT GAA TTA AAT       1152
Pro Val Pro Gly Gly Phe Arg Val Ala Leu Lys Thr Phe Glu Leu Asn
370                 375                 380

GGA TAC CAG ATT CCC AAG GGC TGG AAT GTT ATC TAC AGT ATC TGT GAT       1200
Gly Tyr Gln Ile Pro Lys Gly Trp Asn Val Ile Tyr Ser Ile Cys Asp
385                 390                 395                 400

ACT CAT GAT GTG GCA GAG ATC TTC ACC AAC AAG GAA GAA TTT AAT CCT       1248
Thr His Asp Val Ala Glu Ile Phe Thr Asn Lys Glu Glu Phe Asn Pro
                405                 410                 415

GAC CGA TTC AGT GCT CCT CAC CCA GAG GAT GCA TCC AGG TTC AGC TTC       1296
Asp Arg Phe Ser Ala Pro His Pro Glu Asp Ala Ser Arg Phe Ser Phe
            420                 425                 430

ATT CCA TTT GGA GGA GGC CTT AGG AGC TGT GTA GGC AAA GAA TTT GCA       1344
Ile Pro Phe Gly Gly Gly Leu Arg Ser Cys Val Gly Lys Glu Phe Ala
        435                 440                 445

AAA ATT CTT CTC AAA ATA TTT ACA GTG GAG CTG GCC AGG CAT TGT GAC       1392
Lys Ile Leu Leu Lys Ile Phe Thr Val Glu Leu Ala Arg His Cys Asp
450                 455                 460

TGG CAG CTT CTA AAT GGA CCT CCT ACA ATG AAA ACC AGT CCC ACC GTG       1440
Trp Gln Leu Leu Asn Gly Pro Pro Thr Met Lys Thr Ser Pro Thr Val
465                 470                 475                 480

TAT CCT GTG GAC AAT CTC CCT GCA AGA TTC ACC CAT TTC CAT GGG GAA       1488
Tyr Pro Val Asp Asn Leu Pro Ala Arg Phe Thr His Phe His Gly Glu
                485                 490                 495

ATC TGA                                                                1494
Ile
```

(2) INFORMATION FOR SEQ ID NO:6:

(i) SEQUENCE CHARACTERISTICS:
        (A) LENGTH: 20 amino acids

```
          (B) TYPE: amino acid
          (C) STRANDEDNESS: single
          (D) TOPOLOGY: linear (xi) SEQUENCE DESCRIPTION: SEQ ID NO:6:

Pro Phe Gly Gly Gly Pro Arg Leu Cys Pro Gly Tyr Glu Leu Ala Arg
 1               5                  10                  15

Val Ala Leu Ser
            20

(2) INFORMATION FOR SEQ ID NO:7:

(i) SEQUENCE CHARACTERISTICS:
          (A) LENGTH: 20 amino acids
          (B) TYPE: amino acid
          (C) STRANDEDNESS: single
          (D) TOPOLOGY: linear (xi) SEQUENCE DESCRIPTION: SEQ ID NO:7:

Pro Phe Ser Gly Gly Ala Arg Asn Cys Ile Gly Lys Gln Phe Ala Met
 1               5                  10                  15

Ser Glu Met Lys
            20

(2) INFORMATION FOR SEQ ID NO:8:

(i) SEQUENCE CHARACTERISTICS:
          (A) LENGTH: 20 amino acids
          (B) TYPE: amino acid
          (C) STRANDEDNESS: single
          (D) TOPOLOGY: linear (xi) SEQUENCE DESCRIPTION: SEQ ID NO:8:

Pro Phe Ser Gly Gly Ala Arg Asn Cys Ile Gly Lys Gln Phe Ala Met
 1               5                  10                  15

Asn Glu Leu Lys
            20

(2) INFORMATION FOR SEQ ID NO:9:

(i) SEQUENCE CHARACTERISTICS:
          (A) LENGTH: 20 amino acids
          (B) TYPE: amino acid
          (C) STRANDEDNESS: single
          (D) TOPOLOGY: linear (xi) SEQUENCE DESCRIPTION: SEQ ID NO:9:

Pro Phe Gly Thr Gly Pro Arg Asn Cys Ile Gly Met Arg Phe Ala Ile
 1               5                  10                  15

Met Asn Met Lys
            20

(2) INFORMATION FOR SEQ ID NO:10:

(i) SEQUENCE CHARACTERISTICS:
          (A) LENGTH: 20 amino acids
          (B) TYPE: amino acid
          (C) STRANDEDNESS: single
          (D) TOPOLOGY: linear (xi) SEQUENCE DESCRIPTION: SEQ ID NO:10:

Pro Phe Ser Gly Gly Ser Arg Asn Cys Ile Gly Lys Gln Phe Ala Met
 1               5                  10                  15

Asn Glu Leu Lys
            20
```

(2) INFORMATION FOR SEQ ID NO:11:

(i) SEQUENCE CHARACTERISTICS:
        (A) LENGTH: 351 base pairs
        (B) TYPE: nucleic acid
        (C) STRANDEDNESS: single
        (D) TOPOLOGY: linear (xi) SEQUENCE DESCRIPTION: SEQ ID NO:11:

```
GAACTCCTCT TTGGAGGACA CGAAACCACG GCCAGTGCAG CCACATCTCT GATCACTTAC      60

CTGGGGCTCT ACCCACATGT TCTCCAGAAA GTGCGAGAAG AGCTGAAGAG TAAGGGTTTA     120

CTTTGCAAGA GCAATCAAGA CAACAAGTTG GACATGGAAA TTTTGGAACA ACTTAAATAC     180

ATCGGGTGTG TTATTAAGGA GACCCTTCGA CTGAATCCCC CAGTTCCAGG AGGGTTTCGG     240

GTTGCTCTGA AGACTTTTGA ATTAAATGGA TACCAGATTC CCAAGGGCTG GAATGTTATC     300

TACAGTATCT GTGATACTCA TGATGTGGCA GAGATCTTCA CCAACAAGGA A              351
```

(2) INFORMATION FOR SEQ ID NO:12:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:12:

```
TTTTTTTTTT TTGG                                                       14
```

(2) INFORMATION FOR SEQ ID NO:13:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:13:

```
TTTTTTTTTT TTGA                                                       14
```

(2) INFORMATION FOR SEQ ID NO:14:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:14:

```
TTTTTTTTTT TTGT                                                       14
```

(2) INFORMATION FOR SEQ ID NO:15:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:15:

```
TTTTTTTTTT TTGC                                                       14
```

(2) INFORMATION FOR SEQ ID NO:16:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (xi) SEQUENCE DESCRIPTION: SEQ ID NO:16:

TTTTTTTTTT TTAG                                                    14

(2) INFORMATION FOR SEQ ID NO:17:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:17:

TTTTTTTTTT TTAA                                                    14

(2) INFORMATION FOR SEQ ID NO:18:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:18:

TTTTTTTTTT TTAT                                                    14

(2) INFORMATION FOR SEQ ID NO:19:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:19:

TTTTTTTTTT TTAC                                                    14

(2) INFORMATION FOR SEQ ID NO:20:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:20:

TTTTTTTTTT TTCG                                                    14

(2) INFORMATION FOR SEQ ID NO:21:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:21:

TTTTTTTTTT TTCA                                                    14

(2) INFORMATION FOR SEQ ID NO:22:

(i) SEQUENCE CHARACTERISTICS:

(A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:22:

TTTTTTTTTT TTCT                                                              14

(2) INFORMATION FOR SEQ ID NO:23:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:23:

TTTTTTTTTT TTCC                                                              14

(2) INFORMATION FOR SEQ ID NO:24:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:24:

AAGCGACCGA                                                                   10

(2) INFORMATION FOR SEQ ID NO:25:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:25:

TGTTCGCCAG                                                                   10

(2) INFORMATION FOR SEQ ID NO:26:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:26:

TGCCAGTGGA                                                                   10

(2) INFORMATION FOR SEQ ID NO:27:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (xi) SEQUENCE DESCRIPTION: SEQ ID NO:27:

GGCTGCAAAC                                                                   10

(2) INFORMATION FOR SEQ ID NO:28:

(i) SEQUENCE CHARACTERISTICS:
        (A) LENGTH: 10 base pairs

```
            (B) TYPE: nucleic acid
            (C) STRANDEDNESS: single
            (D) TOPOLOGY: linear (xi) SEQUENCE DESCRIPTION: SEQ ID NO:28:

CCTAGCGTTG                                                                    10

(2) INFORMATION FOR SEQ ID NO:29:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (xi) SEQUENCE DESCRIPTION: SEQ ID NO:29:

GTAGCGGCCG CTGCCAGTGG A                                                       21

(2) INFORMATION FOR SEQ ID NO:30:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (xi) SEQUENCE DESCRIPTION: SEQ ID NO:30:

GTAGCGGCCG CT                                                                 12
```

RETINOID METABOLIZING PROTEIN

This application is a continuation-in-part application of U.S. patent application Ser. No. 08/667,546, filed Jun. 21, 1996, now abandoned.

BACKGROUND OF THE INVENTION

Vitamin A metabolism gives rise to several active forms of retinoic acid (RA) which are involved in regulating gene expression during development, regeneration, and in the growth and differentiation of adult epithelial tissues [Maden, 1992; Chambon, 1995; Mangelsdorf, 1995].

Retinoic acid itself has been found to be useful therapeutically, notably in the treatment of cancers, including acute promyelocytic leukemia (APL), tumors of the head and neck, and skin cancer, as well as in the treatment of skin disorders such as the premalignancy associated actinic keratoses, acne, psoriasis and ichthyosis. Unfortunately, a progressive resistance to RA has been observed in the treatment of APL [Muindi, 1992] and this has been attributed to increased RA metabolism [see Muindi, 1992; and Muindi, 1994 for review]. Therapeutic administration of RA can result in a variety of undesirable side effects and it is therefore important to establish and maintain the minimal requisite doses of RA in treatment. For example, RA treatments during pregnancy can lead to severe teratogenic effects on the fetus. Adverse reactions to RA treatment also include headache, nausea, chelitis, facial dermatitis, conjunctivitis, and dryness of nasal mucosa. Prolonged exposure to RA can cause major elevations in serum triglycerides and can lead to severe abnormalities of liver function, including hepatomegaly, cirrhosis and portal hypertension.

Many laboratory studies have involved metabolites of RA, particularly the activities of all-trans and 9-cis RA metabolites. The mechanism of conversion between all-trans RA and 9-cis RA in vivo is unclear; the asymmetric distribution of these metabolites in developing embryos suggests that they may be preferentially sequestered or generated by tissue specific isomerases [Creech Kraft, 1994]. The normal balance of these metabolites is dependent upon rate of formation from metabolic precursors, retinol and retinaldehyde [Lee, 1990], and rate of catabolism. RA catabolism is thought to proceed through the formation of polar intermediates, including 4-hydroxy-retinoic acid (4-OH-RA) and 4-oxo-retinoic acid (4-oxo-RA) [Frolik, 1979]. It is unknown whether the 4-oxo- and 4-OH-metabolites are simply intermediates in the RA catabolic pathway or whether they can also have specific activities which differ from those of all-trans RA and 9-cis RA. Pijnappel et al. [Pijnappel, 1993] have shown that, in Xenopus, 4-oxo-RA can efficiently modulate positional specification in early embryos and exhibits a more potent ability to regulate Hoxb-9 and Hoxb-4 gene expression than all-trans RA. 4-oxo-RA has been found to bind to retinoic acid receptor-β (RAR-β) with affinity comparable to all-trans RA [Pijnappel, 1993] but poorly to RAR-γ [Reddy, 1992], suggesting that this metabolite exhibits some receptor selectivity. 4-oxo-RA also binds to cellular retinoic acid binding protein (CRABP) but with an affinity slightly lower than that of all-trans RA [Fiorella, 1993]. Takatsuka et al. [Takatsuka, 1996] have shown that growth inhibitory effects of RA correlate with RA metabolic activity but it is unknown whether there is a causal relationship between production of RA metabolites and growth inhibition.

The generation of 4-oxo-RA and 4-OH-RA metabolites is believed to be a cytochrome P450 dependent process. This is because of an observed effectiveness of general P450 inhibitors such as ketoconazole and liarozole in inhibiting the production of these metabolites from RA [Williams, 1987; Van Wauwe, 1992; Van Wauwe, 1988; Van Wauwe, 1990]. In certain tissues (testis, skin, lung) and cell lines (NIH 3T3, HL 60, F9, MCF-7) RA metabolism can be induced by RA pretreatment [Roberts, 1979a & b; Frolik, 1979; Duell, 1992; Wouters, 1992; Takatsuka, 1996]. Studies involving targetted disruption of RAR genes in F9 cells suggest that RAR-α and RAR-γ isoforms may play a role in regulating the enzymes responsible for this increased metabolism [Boylan, 1995].

It has recently been shown that 4-oxoretinol (4-oxo-ROL) can have greater biological activity than retinol. The 4-oxo-ROL is inducible by RA in F9 and P19 mouse teratocarcinoma cells [Blumberg et al., 1995; Achkar et al., 1996].

It is known that zebrafish fins regenerate through an RA sensitive process which utilizes many gene regulatory pathways involved in early vertebrate development [White, 1994; Akimenko, 1995a & b].

As far as the inventors are aware, cytochrome P450s involved in the metabolism of RA in extrahepatic tissues remain uncharacterized at the molecular level.

SUMMARY OF THE INVENTION

The present inventors are the first to identify, clone and sequence a gene (cDNA) encoding a retinoic acid-inducible, retinoic acid-metabolizing protein, including a cDNA which is RA-inducible in humans. The protein has been found to be expressed in epithelia.

A cDNA has been isolated from zebra fish and sequenced. A protein encoded by the cDNA has been expressed and shown to have the ability to hydroxylate retinoic acid at the 4 position of the β-ionone ring of retinoic acid. The protein has been found to be inducible in epithelial cells exposed to retinoic acid.

A human cDNA encoding a protein with similar functionality has also been isolated and sequenced. Homology between sequences from the two species, be they nucleic acids encoding the protein, or the amino acid sequences of the proteins, has been found to be relatively high and both proteins contain a heme-binding motif characteristic of the group of proteins known as cytochrome P450s. The overall homology between the amino acid sequences of these newly obtained proteins and known cytochrome P450s is less than 30%. Notwithstanding this relatively low overall homology, a higher degree of homology has been observed in the heme binding region for certain other P450s. For example, homology between the approximately 20 amino acids defining respective heme binding regions of the new zebrafish protein and CYP4503A12 is about 50% and between the new zebrafish protein and hCYTFAOH is 65%. The homology between the heme binding region itself of a protein of the present invention and another P450 could well be 70%, 75%, 80%, 85%, 90%, 95% or even 100%.

A first aspect of the present invention is thus a purified protein having the ability to oxidize a retinoid, and having an amino acid sequence which is at least about 30% conserved in relation to the amino acid sequence identified as SEQ ID NO:2 or identified as SEQ ID NO:4, or a functionally equivalent homolog thereof. The amino acid sequence identified as SEQ ID NO:2 is of the protein, termed here "zP450RAI", obtained from zebrafish. The amino acid sequence of the human protein is identified as SEQ ID NO:4 and the protein is referred to herein as "hP450RAI".

Such a protein which is at least about 35% conserved in relation to the amino acid sequence identified as SEQ ID NO:2 or identified as SEQ ID NO:4, or a functionally equivalent homolog thereof, also forms part of the invention disclosed herein. Likewise, the degree of sequence conservation of a protein could be 40%, 45%, 50%, 55%, 60%, 65%, 70%, 75%, 80%, 85%, 90%, 95% or of course 100% of either SEQ ID NO:2 or SEQ ID NO:4 or a functionally equivalent homolog thereof, variants being possible so long as the ability of the native protein to oxidize a retinoid is retained. Also within the scope of the invention is any such protein which has the ability to hydroxylate retinoic acid at the 4 position of the β-ionone ring. Of course, conservatively substituted variants of proteins disclosed are within the scope of the present invention.

A retinoid oxidized by a protein of the present invention may be a retinoic acid or a retinol and the protein may have the ability to oxidize the carbon occupying the 4-position of the β-ionone ring of the retinoid. In particular, all-trans retinoids may be metabolized by proteins of the present invention.

In the context of this specification, the term "conserved" describes similarity between sequences. The degree of conservation between two sequences can be determined by optimally aligning the sequences for comparison, as is commonly known in the art, and comparing a position in the first sequence with a corresponding position in the second sequence. When the compared positions are occupied by the same nucleotide or amino acid, as the case may be, the two sequences are conserved at that position. The degree of conservation between two sequences is often expressed, as it is here, as a percentage representing the ratio of the number of matching positions in the two sequences to the total number of positions compared.

The generic term "retinoids" means a group of compounds which includes retinoic acid, vitamin A (retinol) and a series of natural and synthetic derivatives that can exert profound effects on development and differentiation in a wide variety of systems.

In another aspect, the present invention is an isolated nucleic acid molecule encoding a protein of the present invention.

The present invention thus includes an isolated nucleic acid molecule encoding a protein having an amino acid sequence which is at least about 30% conserved in relation to the amino acid sequence identified as SEQ ID NO:2 or identified as SEQ ID NO:4, or a functionally equivalent homolog thereof, for example, or a nucleic acid strand capable of hybridizing with the nucleic acid molecule under stringent hybridization conditions. Of course, the degree of conservation of the protein which the nucleic acid encodes can be higher, that is, 35%, 40%, 45%, 50%, 55%, 60%, 65%, 70%, 75%, 80%, 85%, 90%, 95% or more.

Particularly, the invention is an isolated nucleic acid molecule encoding a protein having the ability to oxidize a retinoid at the carbon occupying the 4-position of the β-ionone ring of the retinoid ring, and more particularly, having all-trans retinoic acid 4-hydroxylase activity. For the purposes of this invention, the term "isolated" refers to a nucleic acid that is substantially free of other cellular material or culture medium when produced by recombinant DNA techniques, or chemical precursors or other chemicals when produced by chemical synthesis.

Cellular expression of preferred proteins of the present invention, preferred embodiments being described in more detail below, can for certain types of cells be induced by exposure of the cells to a retinoid, particularly, retinoic acid. A protein of the present invention, when described as being a "retinoic acid inducible protein", is a protein normally encoded by DNA of a cell and whose expression by that cell can be induced by exposure of the cell to retinoic acid. It will be appreciated that not every cell, even if it contains DNA encoding such a protein, possesses all the attributes necessary to express the protein on exposure to RA. It will be appreciated, however, that the DNA sequence encoding such a protein will occur in some proximity to a regulatory sequence which is necessary to cellular expression of the protein as it occurs in nature. That is, it is expected that RA induces expression of the gene through mediation of at least one regulatory element. It will be appreciated that, given the sequences described herein and modern genetic engineering techniques, a person skilled in the art would be capable of obtaining purified proteins of the present invention without the need for the regulatory sequence. In one respect, the present invention is thus a microbial cell containing and expressing heterologous DNA encoding a retinoic acid inducible protein having all-trans retinoic acid 4-hydroxylase activity.

The sequence of a nucleic acid molecule of the present invention can correspond to a part of a human genome or of a fish genome, or vary therefrom due to the degeneracy of the genetic code. More particularly, a nucleic acid molecule of the present invention can be a DNA molecule having the sequence identified as SEQ ID NO:3 (zP450RAI) or SEQ ID NO:5 (hP450RAI), or the sequence can be one which varies from one of these sequences due to the degeneracy of the genetic code, or it can be a nucleic acid strand capable of hybridizing with at least one of these nucleic acid molecules under high or low stringency hybridization conditions.

"Stringent hybridization conditions" takes on its common meaning to a person skilled in the art here. Appropriate stringency conditions which promote nucleic acid hybridization, for example, 6x sodium chloride/sodium citrate (SSC) at about 45° C. are known to those skilled in the art. The following examples are found in Current Protocols in Molecular Biology, John Wiley & Sons, N.Y. (1989), 6.3.1–6.3.6: For 50 ml of a first suitable hybridization solution, mix together 24 ml formamide, 12 ml 20x SSC, 0.5 ml 2 M Tris-HCl pH 7.6, 0.5 ml 100x Denhardt's solution, 2.5 ml deionized $H_2O$, 10 ml 50% dextran sulfate, and 0.5 ml 10% SDS. A second suitable hybridization solution can be 1% crystalline BSA (fraction V), 1 mM EDTA, 0.5 M $Na_2HPO_4$ pH 7.2, 7% SDS. The salt concentration in the wash step can be selected from a low stringency of about 2x SSC at 50° C. to a high stringency of about 0.2x SSC at 50° C. Both of these wash solutions may contain 0.1% SDS. In addition, the temperature in the wash step can be increased from low stringency conditions at room temperature, about 22° C., to high stringency conditions, at about 65° C. The cited reference gives more detail, but appropriate wash stringency depends on degree of homology and length of probe. If homology is 100%, a high temperature (65° C. to 75° C.) may be used. If homology is low, lower wash temperatures must be used. However, if the probe is very short (<100 bp), lower temperatures must be used even with 100% homology. In general, one starts washing at low temperatures (37° C. to 40° C.), and raises the temperature by 3–5° C. intervals until background is low enough not to be a major factor in autoradiography.

Another aspect of this invention is isolated mRNA transcribed from DNA having a sequence encoding a protein of the present invention.

In another aspect, the present invention is isolated DNA having a sequence according to a nucleotide sequence described above operatively linked in a recombinant cloning vector. In the context of this invention, the two-part term "operatively linked" means both that the regulatory sequence contains sufficient element(s) to allow expression of the nucleic acid in question and that the nucleic acid is linked to the regulatory sequence appropriately. For example, the nucleic acid of the invention is in the appropriate orientation and in phase with an initiation codon. The present invention thus includes a stably transfected cell line which expresses a protein having the ability to hydroxylate retinoic acid at the 4 position of the β-ionone ring of retinoic acid. The invention includes a culture of cells transformed with a recombinant DNA molecule having a nucleic acid sequence which encodes a protein having the ability to hydroxylate retinoic acid at the 4 position of the β-ionone ring of retinoic acid.

Another aspect of the present invention is a host cell that has been engineered genetically to produce a protein of the invention described above, the cell having incorporated expressibly therein heterologous DNA encoding said protein. The cell may be selected such that production of the protein is inducible by exposing the cell to a retinoid, preferably, retinoic acid. The cell can be eukaryotic.

The present invention also includes a process for producing an above-described protein of the invention. Such a process includes: preparing a DNA fragment containing a nucleotide sequence which encodes the protein; incorporating the DNA fragment into an expression vector to obtain a recombinant DNA molecule which contains the DNA fragment and is capable of undergoing replication; transforming a host cell with the recombinant DNA molecule to produce a transformant which can express the protein; culturing the transformant to produce the protein; and recovering the protein from resulting cultured mixture.

The present invention includes an antibody to a protein of the invention. Here, the term "antibody" is intended to include a Fab fragment and it can be a monoclonal antibody. The antibody can be specifically to the amino acid sequence identified as SEQ ID NO:4, i.e., hP450RAI.

The present invention includes a purified protein for use in metabolizing retinoic acid in an organism or cell in need of such metabolizing. Likewise, the invention includes a method for metabolizing retinoic acid in an organism or cell in need of retinoic acid metabolizing wherein the method includes administering a protein of the invention as described above.

The invention includes a method for inhibiting retinoic acid hydroxylation in an organism in need of such inhibition, comprising introducing into cells of the organism an effective amount of an antisense RNA or oligonucleotide substantially complementary to at least a portion of the sequence identified as SEQ ID NO:5. The organism can be human and/or the organism can be in need of treatment against a cancerous disease. Such a method can include use of at least one delivery vehicle or technique selected from the set of viral vectors, microinjection, electroporation, coprecipitation, liposomes, aerosol delivery and lavage. The portion of the sequence may be 5 bases in length, between 5 and 50 bases in length, 5 and 30 bases in length between 10 and 20 bases in length, or another suitable length may be found. The organism may be a human patient and the method can include treating the patient against a cancerous disease.

The invention also includes a method of inhibiting retinoic acid hydroxylation in an organism in need of such inhibition by administering to the organism an effective amount of an antibody, such antibodies being described above. A particularly useful antibody for the treatment of a human would be an antibody to the protein having the amino acid sequence identified as SEQ ID NO:4, or a portion thereof. It would be advantageous to adapt such an antibody for administration to a human by "humanizing" the antibody, as is understood by those skilled in the art [Hozumi, 1993].

The invention includes a method for producing a desired protein, comprising providing a cell which can produce an endogenous protein in response to exposure to a retinoid; incorporating into DNA of the cell a DNA sequence encoding for the desired protein at or near a site which is normally occupied by a DNA sequence encoding for the endogenous protein; and exposing the cell to the retinoid so as to induce production of the desired protein.

In another embodiment, the present invention is a kit for determining the presence of a protein having the ability to oxidize a retinoid, and having an amino acid sequence which is at least about 30% conserved in relation to the amino acid sequence identified as SEQ ID NO:2 or identified as SEQ ID NO:4, or more likely for determining the presence of a protein having an amino acid sequence identified as SEQ ID NO:4. The kit includes an antibody to the protein linked to a reporter system wherein the reporter system produces a detectable response when a predetermined amount of the protein and the antibody are bound together.

In another aspect, the present invention is a kit for determining the presence of a nucleic acid encoding a protein of invention, or a nucleic acid strand capable of hybridizing with the nucleic acid under stringent hybridization conditions, or having the sequence identified as SEQ ID NO:3 or SEQ ID NO:5, or which varies from the sequence due to the degeneracy of the genetic code, or a nucleic acid strand capable or hybridizing with at least one said nucleic acid under stringent hybridization conditions. The kit includes a nucleic acid molecule capable of hybridizing with at least a portion of a said nucleic acid or nucleic acid strand under stringent conditions in which the nucleic acid molecule is linked to a reporter system wherein the reporter system produces a detectable response when a predetermined amount of the nucleic acid or nucleic acid strand and nucleic acid molecule are hybridized with each other. The molecule can be 5 bases in length or longer; between 5 and 50 bases in length, 5 and 40 or 30 bases in length, or between 10 and 20 bases in length. Of course it might be possible to find a more suitable base length.

BRIEF DESCRIPTION OF THE DRAWINGS

FIG. 2(c) shows an amino acid sequence (SEQ ID NO:2) corresponding to cDNA (492 amino acid open reading frame). The boxed residues indicate the heme-binding motif characteristic of cytochrome P450s.

FIG. 2(d) shows amino acid sequence comparisons between zP450RAI and several other cytochrome P450s (SEQ ID Nos: 6,7,8,9,10) in the area of the conserved heme-binding motif found in the superfamily. The cysteine, designated 0 in the figure, which has been shown to be directly involved in heme-binding [Gotoh, 1989] is surrounded by several highly conserved amino acids.

FIG. 4 shows elution profiles of lipid soluble extracts obtained from treated media of pSG5-zP450RAI transfected COS-1 cells and pSG5 transfected control cells.

FIGS. 4(a) and 4(b) are plots of cpm vs fraction number for cells incubated with 575 pM [11,12-$^3$H]RA for 4 hours and 24 hours, respectively, pSG5-zP450RAI COS-1 cells (———) and control cells (---). Metabolism of [11,12-$^3$H]RA to total aqueous soluble metabolites was measured using aliquots of the aqueous soluble extract subjected to β-scintillation counting. See insets of FIGS. 4(a) and (b).

FIGS. 4(c) and 4(d) are plots of absorbance vs retention time for cells incubated with 1 μM RA for 4 and 24 hours, respectively. Peaks observed in zP450RAI transfected cell are shaded black. The region of the chromatogram from 4 to 6 min has been expanded (see insets of FIGS. 4(c) and (d)). In cells transfected with zP450RAI cDNA, the generation of peaks corresponding to 4-oxo and 4-OH was observed.

FIG. 9 shows the zebrafish amino acid sequence (bottom row: SEQ ID NO:2) of zP450RAI aligned with the human P450RAI amino acid sequence (top row; SEQ ID NO:4).

DESCRIPTION OF PREFERRED EMBODIMENTS

Figure 1:
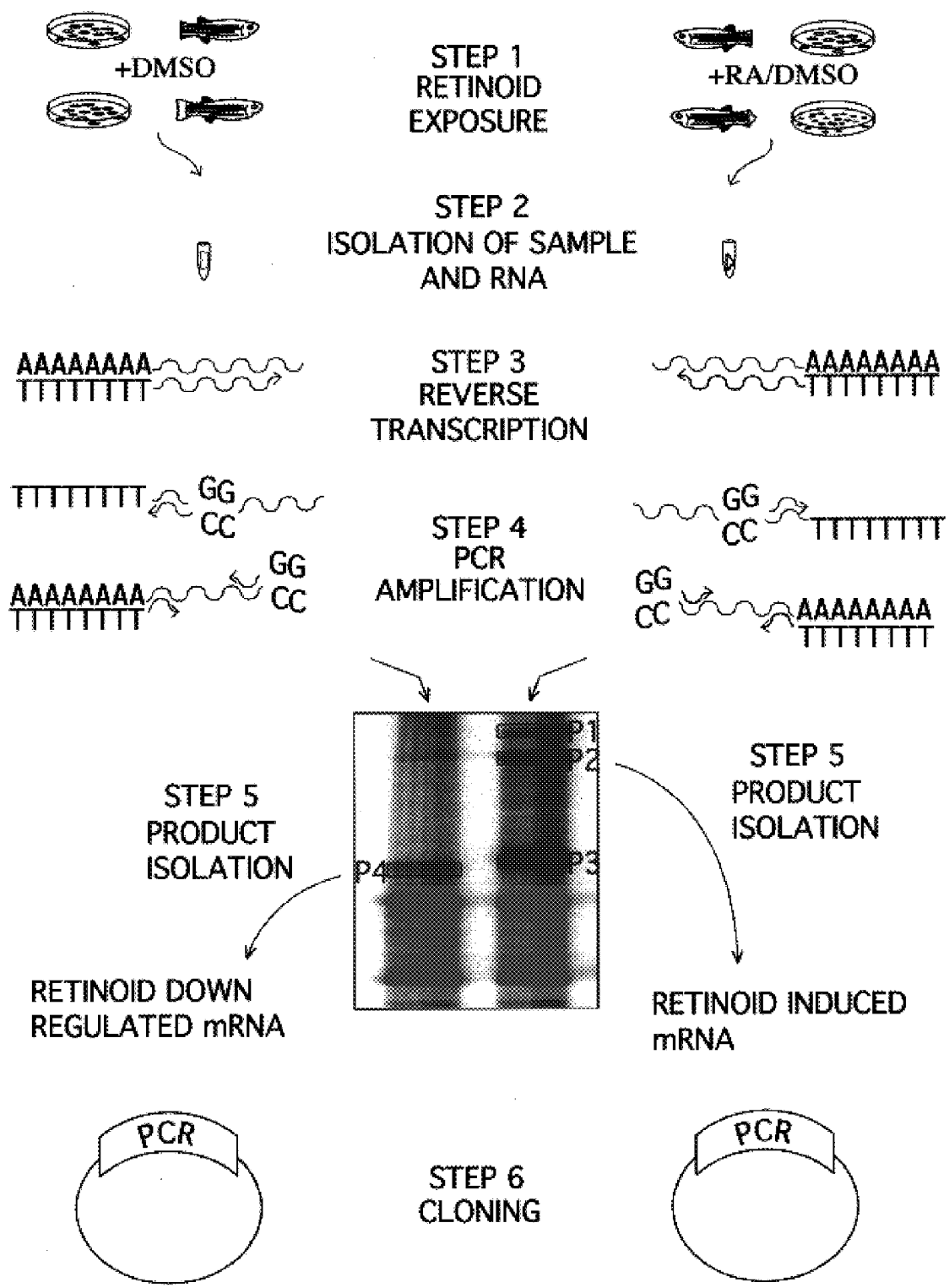
FIG. 1 is a schematic representation of the steps used to isolate retinoid-regulated genes using differential display of mRNA.

FIG. 1 outlines the steps used to isolate retinoid-regulated genes using differential display of mRNA. The cloned products isolated in step 6 of FIG. 1 were used for sequencing and screening of *Danio rerio* (*D. rerio*) cDNA libraries. P1, P2 and P3 correspond to fragments from RA induced mRNAs. P4 is a PCR product from a down-regulated mRNA. Details of procedures followed in determination of gene sequences described herein follow.

*Danio rerio* Stocks

*D. rerio* were kept at 28.5° C. in 40 L tanks with 25–30 fish per tank on a 14 hour light-10 hour dark cycle. Tap water was conditioned by the addition of 10 ml of Water Conditioner (Sera Aqutan) and 10 ml of 250 g/L Aquarium Salt (Nutra Fin) per 20 L. 2–3 L of water was changed daily. Amputation of fins was carried out following anaesthetization of the fish in a solution of 0.2% ethyl-m-aminobenzoate methanesulfonic acid (ICN) in conditioned water. Retinoic acid treatment was performed by adding all-trans RA, to a final concentration of $10^{-6}$M, directly into the tank water two days following amputation. Both control- and RA-treated fish were kept in the dark during the experiments.

Differential Display of mRNAs

Differential mRNA display was performed essentially as described by Liang and Pardee (1992) with appropriate modifications as described herein. Regenerating tissues were collected 3 days post-amputation (24 hours post-RA addition) and quick frozen in liquid nitrogen. Poly $(A)^+$ RNA was isolated using the Micro Fast-Track kit. Duplicate independent reverse transcription reactions were performed on the isolated poly$(A)^+$ RNA from both the treated and untreated samples for each specific 3' poly-T primer used (5'-$T_{12}$VN-3'). The symbol "V" represents A or C or G and not T or U. Several combinations of the 3' poly-T primers given in the first column of Table 1 and the upstream primers given in the second column were utilized for PCR amplification. For each reaction 0.1 μg poly$(A)^+$ RNA was reverse transcribed in a 20 μl reaction volume containing 300U Superscript Reverse Transcriptase (Gibco/BRL), 1× Buffer, 20 μM each dGTP, dATP, dCTP and dTTP, 10 μM dithiothreitol (DTT) and 5 pmol of 5'-$T_{12}$VN-3' primer. The reactions were mixed and incubated at 35° C. for 60 minutes, followed by 5 minutes at 95° C. PCR amplification was performed in a Perkin Elmer Cetus PCR machine as follows: 1 μl cDNA synthesis reaction, 5U Taq DNA polymerase (Gibco/BRL), 1× PCR Buffer, 2 μM each DGTP, dATP, dCTP and dTTP, 10 μCi α-[$^{35}$S]dATP (redivue, Amersham) 1.2 MM MgCl$_2$, 0.5 μM upstream primer and 0.5 μM of the corresponding 5'-$T_{12}$VN-3' primer. PCR conditions were as follows: 1 cycle, 94° C. for 5 minutes; 40 cycles, 94° C. for 30 seconds, 42° C. for 1 minute, 72° C. for 30 seconds; followed by a final extension of 5 minutes at 72° C. 4 μl of the PCR reactions were loaded o nto a 6% non-denaturing polyacrylamide gel and electrophoresed at 60 watts, 45° C. The gel was dried and exposed for 12 to 24 hours on Kodak XAR film at room temperature. 1

TABLE 1

Sequences of the downstream Poly (T) oligonucleotides for the differential display procedure.

| 3'-Poly(T) primers: | 5'-degenerate primers: |
|---|---|
| 5'-TTT.TTT.TTT.TTT.GG-3' | 5'-AAG.CGA.CCG.A-3' |
| 5'-TTT.TTT.TTT.TTT.GA-3' | 5'-TGT.TCG.CCA.G-3' |
| 5'-TTT.TTT.TTT.TTT.GT-3' | 5'-TGC.CAG.TGG.A-3' |
| 5'-TTT.TTT.TTT.TTT.GC-3' | 5'-GGC.TGC.AAA.C-3' |
|  | 5'-CCT.AGC.GTT.G-3' |
| 5'-TTT.TTT.TTT.TTT.AG-3' | |
| 5'-TTT.TTT.TTT.TTT.AA-3' | |
| 5'-TTT.TTT.TTT.TTT.AT-3' | |
| 5'-TTT.TTT.TTT.TTT.AC-3' | |
| 5'-TTT.TTT.TTT.TTT.CG-3' | |
| 5'-TTT.TTT.TTT.TTT.CA-3' | |
| 5'-TTT.TTT.TTT.TTT.CT-3' | |
| 5'-TTT.TTT.TTT.TTT.CC-3' | |

0

In Table 1, the sequences in the first column are identified as SEQ ID NOs: 12, 13, 14, 15, 16, 17, 18, 19, 20, 21, 22 and 23, respectively. The sequences in the second column are identified as SEQ ID NOs: 24, 25, 26, 27 and 28, respectively.

Gel Purification and Reamplification

Bands demonstrating reproducible differential amplifications (see FIG. 2a) were found for the upstream-downstream primer combination of 5'-TGCCAGTGGA-3'-poly-T primer, 5'-TTT TTT TTT TTT AG-3' (SEQ ID NOs: 26 and 16, respectively). These bands were excised from the gel by overlaying the X-ray film and cutting out the corresponding piece of dried gel and filter paper. The PCR product corresponding to a fragment of the protein described herein was isolated from the band in FIG. 2(a). Samples were placed in 100 μl of nuclease free water, incubated for 10 minutes at room temperature, then boiled for 15 minutes. The supernatant was recovered following a 15 minute centrifugation at 12,000×g.

In order to facilitate cloning of the PCR products, several changes were made to the reactions. Primers which included EagI restriction endonuclease sites were used in the reamplification. Based on results obtained in the differential display analysis, the upstream 5'-TGCCAGTGGA-3' primer was replaced by 5'-GTAG<u>CGGCCG</u>CTGCCAGTGGA-3' (SEQ ID NO: 29) and the downstream poly-T primer, 5'-TTT TTT TTT TTT AG-3', was replaced by 5'-GTAG <u>CGGCCGCT$_{12-3}$</u>' (SEQ ID NO:30). In addition, the reaction volume was increased to 40 μl, isotope was omitted and 20 as opposed to 40 cycles were performed. 5 μl aliquots of the PCR reactions were removed and the products were visualized by electrophoresis in a 1% agarose gel followed by ethidium bromide staining and UV illumination.

Cloning PCR Products

The reamplified products were purified by phenol/chloroform extraction followed by ethanol precipitation. The resulting DNA pellet was resuspended in 17 μl of sterile water and digested at 37° C. for 1 hour by the inclusion of 10U EagI (New England Biolabs), and 1× NEB 3 buffer. EagI restriction endonuclease was heat inactivated by incubation at 65° C. for 20 minutes. pBluescript SK$^+$ vector was prepared by digestion with EagI, followed by dephosphorylation using calf intestinal alkaline phosphatase (CAP, Promega). Restriction digests were purified using the GeneClean II Kit (Bio 101) following electrophoresis in a 1% agarose gel. In a total ligation volume of 10 μl, 2 μl of digested PCR product, 1 μl digested SK$^+$, 1U T4 DNA ligase (Gibco/BRL) and 1× buffer were incubated at 16° C. overnight. E. coli bacterial strain JM109 was transformed with 1 μl of the ligation product using the BioRad Gene Pulser, then plated on LB+ampicillin plates and incubated overnight at 37° C.

Colony Selection

Individual colonies were transferred in duplicate to fresh LB plates and grown overnight at 37° C. Colonies were transferred to nitrocellulose membrane and denatured in a solution of 1.5M NaCl, 0.5M NaOH for 5 minutes, neutralized in 1.5M NaCl, 0.5M Tris-HCl, pH 8.0 for 5 minutes, followed by two 5 minute washes in 2× SSC. Membranes were then UV cross-linked (Stratalinker UV Crosslinker, Stratagene). Prehybridization and hybridization were performed using Quickhyb (Stratagene) following the manufacturer's directions. Each colony lift was probed with the corresponding PCR product isolated during the gel reamplification and purification step. α-[$^{32}$P]-dATP labelled probes were generated using the Prime-It Kit II (Stratagene). Subsequent to hybridization, filters were washed twice for 20 minutes in 2× SSC, 0.1% SDS solution at room temperature and exposed to Kodak X-omat autoradiography film overnight at −70° C. Positive colonies were selected from the duplicate plates, grown overnight in LB+ampicillin (100 μg/ml) and plasmid DNA isolated using the Qiaprep Spin Plasmid Kit (Qiagen).

Clones were sequenced using the T7 Sequencing Kit (Pharmacia Biotech). Sequence comparisons were generated using the GeneWorks software package (Intelligenetics).

Screening of a D. rerio cDNA Library

A random primed D. rerio 6–18 hour embryo cDNA library constructed in Uni-ZAP II (Stratagene) was produced. $4.5\times10^5$ independent pfu were screened using the random primed, $\alpha$-[$^{32}$P]-dATP labelled 337 bp PCR fragment isolated by mRNA differential display as a probe. Filters were prehybridized for 1–4 hours at 42° C. in 50% formamide, 5× SSPE, 1× Denhardt's solution, 0.2 mg/ml denatured salmon sperm DNA. Hybridization was performed at 42° C. by adding denatured probe to the prehybridization solution. Filters were washed two times for 20 minutes in 2× SSC, 0.05% SDS at room temperature and exposed to Kodak XAR film overnight at −70° C. Positive plaques were picked into 500 μl SM buffer and subjected to additional rounds of rescreening until purified. Positive plaques were exposed to the in vivo excision protocol following the manufacturer's directions (Stratagene). pBluescript containing colonies were plated onto LB+amp plates and grown overnight at 37° C. Sequence data were generated using the T7 Sequencing Kit (Pharmacia) and analysed using the GeneWorks software package (Intelligenetics).

Whole Mount in situ hybridization

RA- and DMSO-treated regenerates were isolated 72 hours post-amputation (24 hours post RA/DMSO addition), washed in PBS and prepared for whole mount in situ hybridization. In situ hybridizations were undertaken as previously described [White, 1994].

Northern Blot Analysis

Fish were allowed to regenerate their caudal fins for 72 hours. At 48 hours $10^{-6}$M all-trans RA in DMSO vehicle or DMSO alone was added directly to the tank water. mRNA was prepared using the Micro Fast-Track mRNA isolation kit (Invitrogen, California) according to the manufacturer's directions. 3.0–5.0 μg poly A$^+$ RNA was electrophoresed, blotted and probed using a previously described method [White, 1994] with the full length zP450RAI cDNA according obtained as described below. Ethidium bromide stained agarose gel showed that equivalent amounts of mRNA were used in the blotting experiments. See lanes 2 and 3 of FIG. 3(a).

HPLC Analysis

Figure 4A:
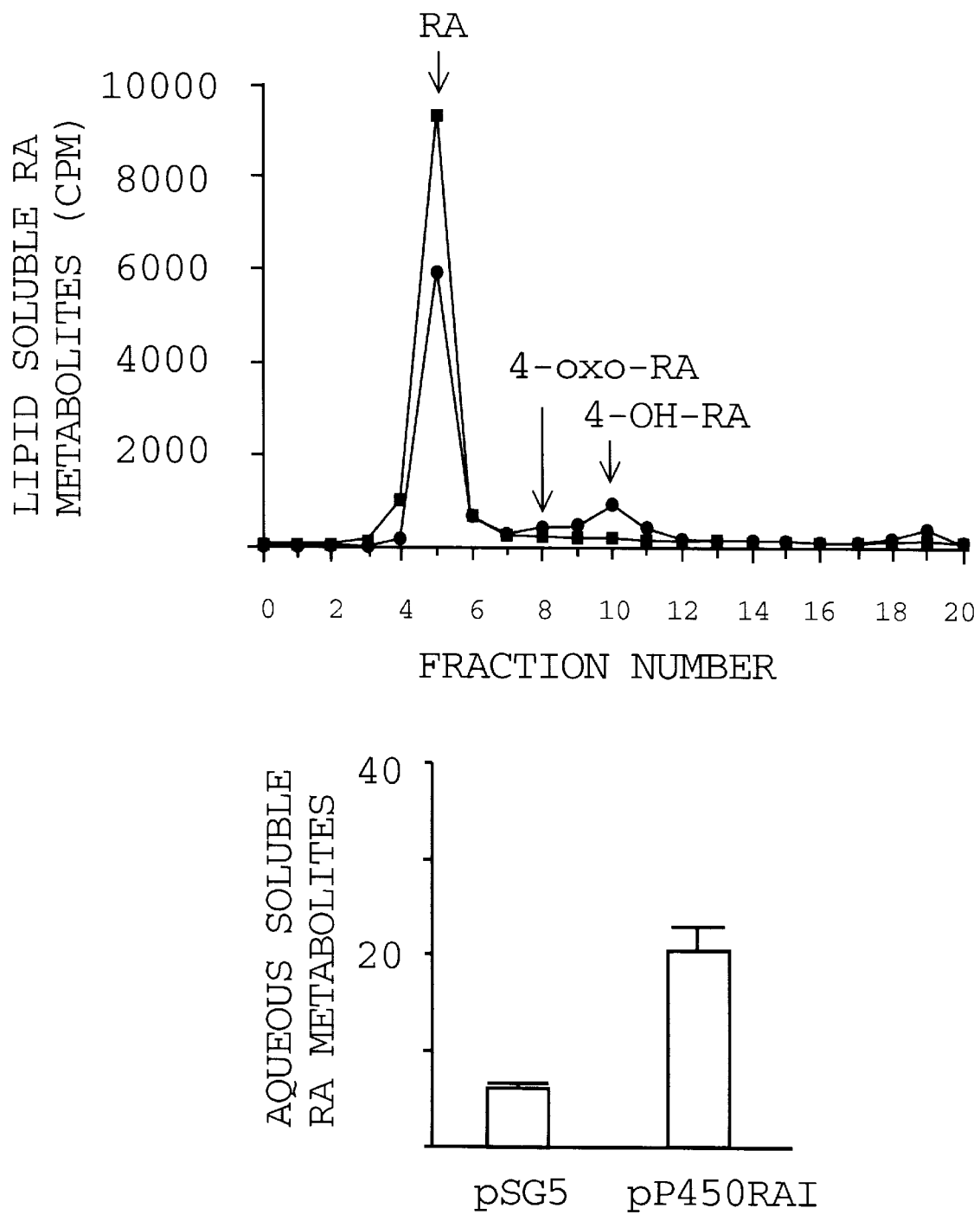

Media from transfected cells incubated with 575 pM [11,12-$^3$H]RA (FIGS. 4(a) and 4(b)) or 1 μM RA (FIGS. 4(c) and 4(d)) for either 4 hrs (FIGS. 4(a) and 4(c)) or 24 hrs (FIGS. 4(b) and 4(d)) were acidified with 0.1% acetic acid. Lipid soluble metabolites were separated from aqueous soluble metabolites using a total lipid extraction of the medium [Bligh, 1957]. Metabolism of [11,12-$^3$H]RA to total aqueous soluble metabolites was measured using aliquots of the aqueous soluble extract subjected to β-scintillation counting (See the insets of FIGS. 4(a) and 4(b)). Lipid soluble extracts were evaporated to dryness under a stream of nitrogen and resuspended in 93.5/5/1/0.5 hexane/isopropanol/methanol/acetic acid (H/I/M/AA). Metabolites were separated by HPLC using a Zorbax-SIL (3μ, 8×0.62 cm) column eluted with a solvent system of 93.5/5/1/0.5 H/I/M/AA at a flow rate of 1 ml/min.

EXAMPLE 1

Characterization of a Novel Cytochrome P450

Figure 2A:
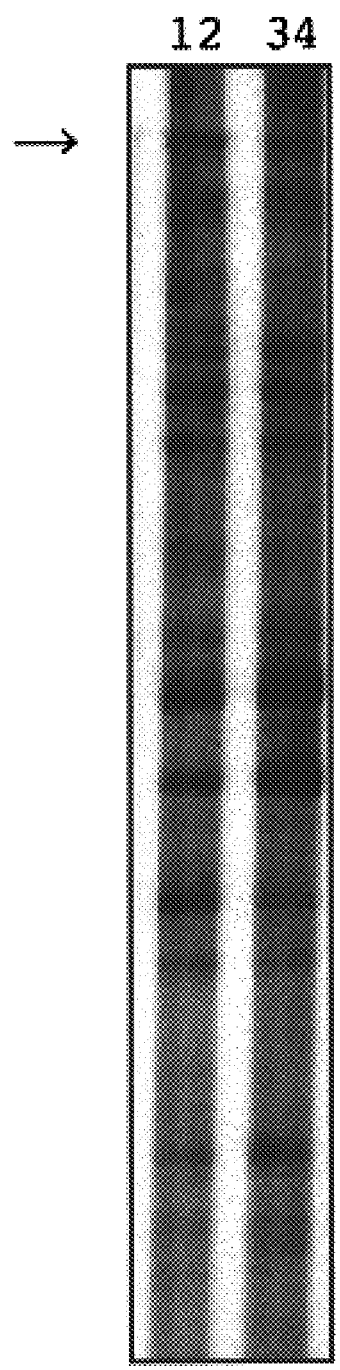
FIG. 2(a) shows a polyacrylamide gel of PCR amplified mRNA in duplicate obtained using retinoic acid-treated fish (lanes 1 and 2) and dimethyl sulfoxide-(DMSO) treated control fish (lanes 3 and 4). The arrow indicates a PCR amplified band present in the RA-treated samples and not observed in the controls.
Figure 2B:
FIG. 2(b) shows the nucleotide sequence (SEQ ID NO:1) of the 337 base pair PCR product isolated from the band (arrow) of FIG. 2(a). The arrows indicate the nucleotide sequences where the upstream and downstream priming sites for differential display PCR amplification were located in the 3'-untranslated portion of zP450RAI.

Transcripts present in fin tissue regenerating in the presence or absence of RA were compared using the differential display PCR technique developed by Liang and Pardee [Liang, 1992] (FIG. 2(a). One of the differential display products which exhibited a dependence on the presence of RA for its expression, indicated by the arrow in FIG. 2(a), was isolated and sequenced. The sequence is identified as SEQ ID NO:1 and is also shown in FIG. 2(b). The amino acid sequence corresponding to the cDNA, termed here, "zP450RAI", is shown in FIG. 2(c) and identified as SEQ ID NO:2. BLAST search analyses revealed sequence homology between zP450RAI and multiple members of the cytochrome P450 superfamily. Alignments between zP450RAI cDNA deduced amino acid sequence and those of other cytochrome P450s indicated that zP450RAI exhibited less than 30% overall amino acid identity with members of previously defined subfamilies [Nelson, 1993]. zP450RAI contains many of the structural motifs which are common to cytochrome P450 family members, including the heme-binding domain located in the C-terminal portion of the protein. See FIG. 2(d).

EXAMPLE 2

Cell Specific Induction of zP450RAI by All-trans RA

Figure 3A:
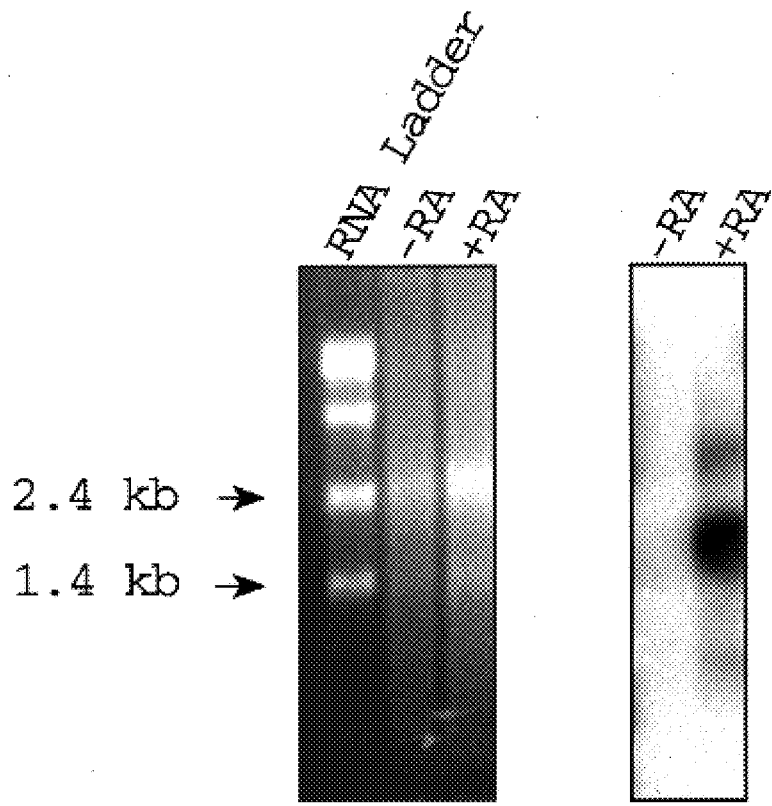
FIG. 3(a) shows Northern blot analysis of mRNAs obtained from regenerate tissue of RA-treated fish in lane 5, and controls (DMSO-treated fish) in lane 4, using a zP450RAI cDNA probe. Comparison to an RNA ladder (lane 1) shows the major zP450RAI transcript to be in the 1.4–2.4 kb range.

Northern blot analysis of mRNAs expressed in regenerate tissue isolated from control (dimethyl sulfoxide-treated) and RA-treated fish was performed with a full-length zP450RAI cDNA probe. zP450RAI transcripts were not detectable in regenerate tissue from control fish (FIG. 3(a), lane 4) but were very noticeably present in tissues isolated from fish exposed to RA for 24 hours (FIG. 3(a), lane 5).

Figure 3B:
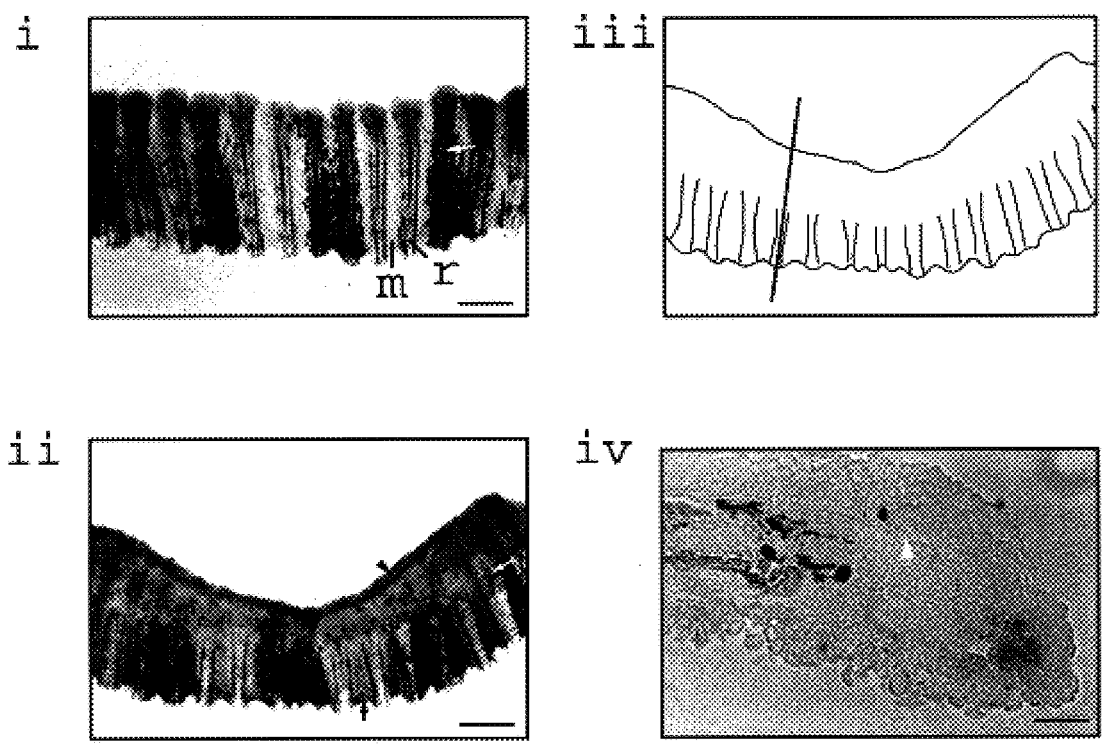
FIG. 3(b) shows localization of zP450RAI transcripts in regenerating caudal fin tissue 72 hours post-amputation by whole mount in situ hybrization. (i) zP450RAI transcripts were found to be undetectable in DMSO-treated regenerates. The original plane of amputation is indicated by the white line with arrowhead; m (soft mesenchyme) and r (bony rays) are labelled. (ii) In a sample obtained from an RA-treated fish, zP450RAI transcripts, indicated by the black arrowhead, were found to be localized to a band of cells extending across the distal tip of the regenerate. Lower levels of expression of zP450RAI were also evident in non-regenerate tissue at the proximal base of the isolated fin, as indicated by the black line with arrowhead. The plane of amputation is indicated by the white line with arrowhead as in FIG. 3(b)(i). (iii) A histological section taken through the plane is indicated by the line. (iv) A histological section of RA-treated fins post-hybridization is shown. Localized expression of zP450RAI was detected in a subset of epithelial cells (black arrowhead) which lie at the distal tip of the regenerate. Basement membrane separating the dense blastemae and the wound epithelium is indicated by the grey arrowhead.

Whole mount in situ hybridization was used to determine the cellular localization of zP450RAI expression in regenerating fin tissue. FIG. 3(b) shows regenerating fins from control and RA-treated fish. zP450RAI transcripts are not detectable in control fin tissue (FIG. 3(b)(i)). In regenerating tissue from RA-treated fish, zP450RAI transcripts were found to be abundant in a layer of epithelial cells extending across the distal edge of the wound epithelium as indicated by the black arrowhead in FIG. 3(b)(ii). Some low level staining was also observed in inter-ray tissue as indicated by the black line with arrowhead in FIG. 3(b)(ii). A histological section of an RA-treated fin, taken along the line shown in FIG. 3(b)(iii), is shown in FIG. 3(b)(iv). The section indicates that cells expressing zP450RAI are located deep within the epithelial layer at the distal tip of the blastemal mesenchyme.

EXAMPLE 3

Metabolism of All-trans RA by zP450RAI Transfected Cells

Retinoic acid as a substrate of zP450RAI was studied. The full-length zebrafish zP450RAI cDNA was cloned into the eukaryotic expression vector pSG5 [Green, 1988]. COS-1 cells were transiently transfected with either pSG5 or pSG5-zP450RAI and then incubated with either picomolar concentrations of [11,12-$^3$H]all-trans-RA or micromolar concentrations of non-radioactive all-trans-RA. COS-1 cells are an African green monkey kidney "fibroblast-like" cell line. zP450RAI expression in COS-1 cells promoted the rapid conversion of RA into both lipid- and aqueous-soluble metabolites. See FIGS. 4(a) and 4(b). Fractions of total lipid extracts of transfected cells were initially separated by normal-phase HPLC on Zorbax-SIL. Comparison between extracts from pSG5 and pSG5-zP450RAI-transfected cells indicated that zP450RAI significantly increased RA metabolism. Incubation of zP450RAI-transfected cells with 575 pM [11,12-$^3$H]all-trans-RA for either 4 or 24 hours resulted in accumulation of RA metabolites, one of which co-migrated on a column with synthetic standards 4-OH-RA and 18-OH-RA, and a second slightly less polar metabolite which co-migrated with 4-oxo-RA standard (FIGS. 4(*a*) and 4(*b*)). Rechromatography of RA metabolites using other HPLC systems confirmed the identity of these two metabolites as 4-OH-RA and 4-oxo-RA (Table 2). It is possible that the aqueous-soluble radioactivity represents glucuronides of RA metabolites or glucuronides of RA itself. Rapid glucuronidation of 4- and 18-hydroxy-RA in mammalian cell extracts has been reported by others [Wouters, 1992; Takatsuka, 1996].

TABLE 2

Chromatographic properties of RA metabolites.

| Metabolite | Retention Time (min) | | |
|---|---|---|---|
| | Z-Sil[a] | Z-CN[b] | Z-ODS[c] |
| RA (std) | 2.57 | 4.47 | 19.92 |
| 4-oxo-RA (std) | 4.79 | 11.33 | 11.73 |
| 4-OH-RA (std) | 5.17 | 9.65 | 12.65 |
| 18-OH-RA (std) | 5.06 | 9.53 | 14.03 |
| Peak 1 (RA) | 2.57 | 4.48 | 19.73 |
| Peak 2 (4-oxo-RA) | 4.87 | 11.38 | 11.57 |
| Peak 3 (4-OH-RA) | 5.16 | 9.68 | 12.68 |

[a]HPLC conditions: Zorbax-SIL column eluted with 93.5/5/1/0.5 H/I/M/A.A. (1 ml/min)
[b]HPLC conditions: Zorbax-CN column eluted with 93.5/5/1/0.5 H/I/M/A.A (1 ml/min)
[c]HPLC conditions: Zorbax-ODS column eluted with a 20 min linear gradient with solvent containing 10 mM ammonium acetate which ranged from 55.45 to 5.95 H$_2$O/MeOH (2 ml/min).

A similar pattern of zP450RAI-dependent metabolism was also observed using a much higher RA concentration (1 $\mu$M). zP450RAI-transfected COS-1 cells incubated for 4 or 24 hours with 1 $\mu$M RA generated two closely-running peaks which were discernible in a 350nm HPLC trace shown in FIGS. 4(*c*) and 4(*d*), but which were essentially undetectable in control pSG5-transfected cells (See the insets of FIGS. 4(*c*) and 4(*d*)). These peaks co-migrated with those of 4-oxo-RA and 4-OH-RA standards, respectively. Diode array spectrophotometric detection of the zP450RAI-generated peaks showed that the spectral properties of the two metabolite peaks matched the standard retinoids [In hexane-based solvents: 4-OH-RA, $\lambda_{max}$=350 nm; 4-oxo-RA, $\lambda_{max}$=355 nm; in methanol-based solvents: 4-OH-RA, $\lambda_{max}$=340 nm; 4-oxo-RA, $\lambda_{max}$=360 nm].

The invention thus includes a retinoic acid metabolizing protein belonging to the family of cytochrome P450s and generation of the protein in zebrafish caudal fin wound epithelium being induced in response to RA treatment. While RA metabolizing activity has previously been detected in epithelial tissues of several species [Frolik, 1979; Roberts, 1979; Wouters, 1992; Duell, 1992], an actual enzyme responsible for such activity has heretofore been unknown.

zP450RAI is up-regulated by RA treatment and apparently this up-regulation occurs in a specific set of cells in the wound epithelium of regenerating zebrafish caudal fins.

It might be of relevance to the regulation of the generation of this enzyme in vivo that experiments with F9 cells where RARs have been selectively ablated indicate that RAR-$\alpha$, and RAR-$\gamma$ might have a role in the regulation of RA metabolism [Boylan, 1995]. The expression of both RAR-$\alpha$ and RAR-$\gamma$ in the regenerating caudal fin is consistent with the possibility that they may be involved in the regulation of P450RAI expression by RA [White, 1994].

EXAMPLE 4

Cloning of Human P450RAI

The amino acid sequence corresponding to the DNA of zebrafish P450RAI (zP450RAI) (SEQ ID NO:2) was used to search an express sequence tag (EST) database. A commercially available EST clone (SEQ ID NO:11) having a high degree of homology with a C-terminal portion of the zP450RAI (from Glu 293 to Phe 411 of SEQ ID NO:2) was purchased (Research Genetics, Huntsville, Ala.). The clone is reportedly from a human infant brain cDNA library (Bento Soares and M. Fatima Bonaldo) and is apparently otherwise unpublished. The purchased clone was sequenced using the T7 sequencing kit (Pharmacia) and sequence data was generated using the Geneworks Software Package (Intelligenetics).

A cDNA library generated from an NT2 cell line treated with retinoic acid is commercially available (Stratagene, cat#939231) and this product was used for further studies. The cDNA library was probed with a nucleic acid having a sequence identified as SEQ ID NO:11. Eleven positively hybridizing clones were isolated and purified according to the manufacturer's directions. Sequence data for these clones were generated using the T7 Sequencing Kit (Pharmacia) and analyzed using the Geneworks package (Intelligenetics). The human DNA sequence is identified as SEQ ID NO:5 and the corresponding polypeptide as SEQ ID NO:4. FIG. 9 shows aligned portions of the amino acid sequence of the zebrafish protein (SEQ ID NO:2) with the amino acid sequence of the human protein (SEQ ID NO:4).

EXAMPLE 5

Transient Tranfection Analysis

Figure 10A:
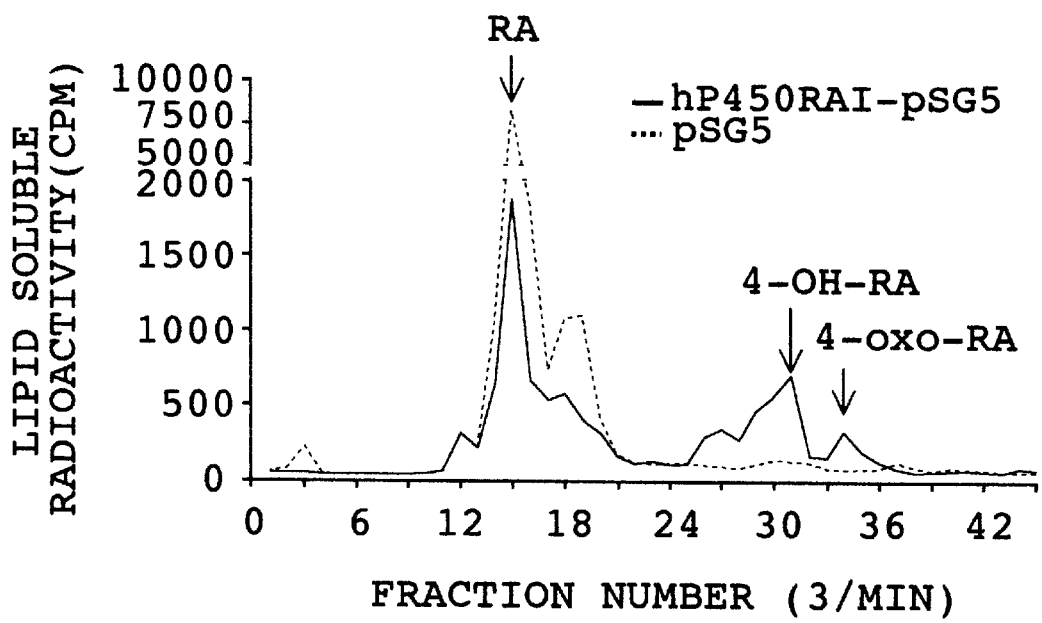
FIG. 10(a) shows elution profiles of lipid soluble extracts obtained from treated media of pSG5-hP450RAI transfected COS-1 cells and pSG5 transfected control cells. Plots of cpm vs fraction number for cells incubated with [11,12-$^3$H]RA for 24 hours of pSG5-hP450RAI COS-1 cells (---) and control cells (———) are shown.
Figure 10B:
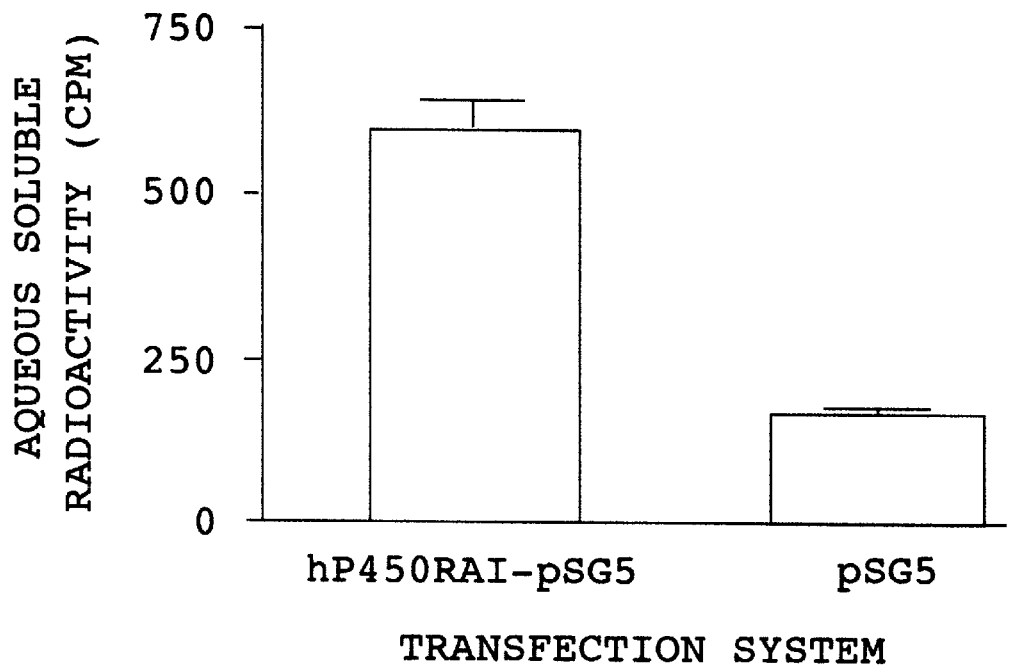
FIG. 10(b) shows measurement of aliquots of the aqueous soluble extract subjected to β-scintillation counting taken to determine metabolism of [11,12-$^3$H]RA to total aqueous soluble metabolites.
Figure 10C:
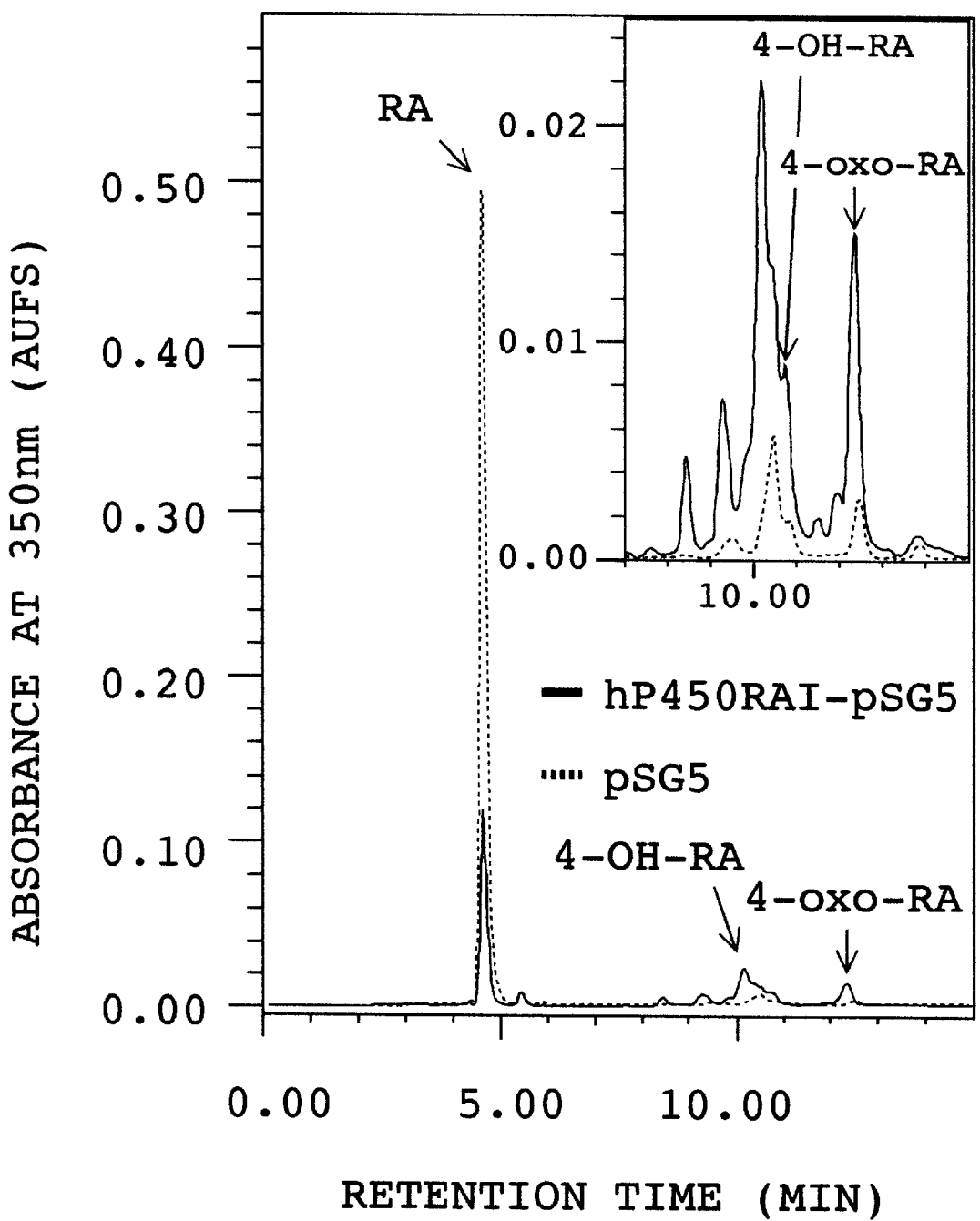
FIG. 10(c) shows plots of absorbance vs retention time for hP450RAI transfected cell (---) and control cells (———) cells incubated with 1 μM RA for 24 hours. The inset is the region around 10 minutes, expanded for clarity.
Figure 11A:
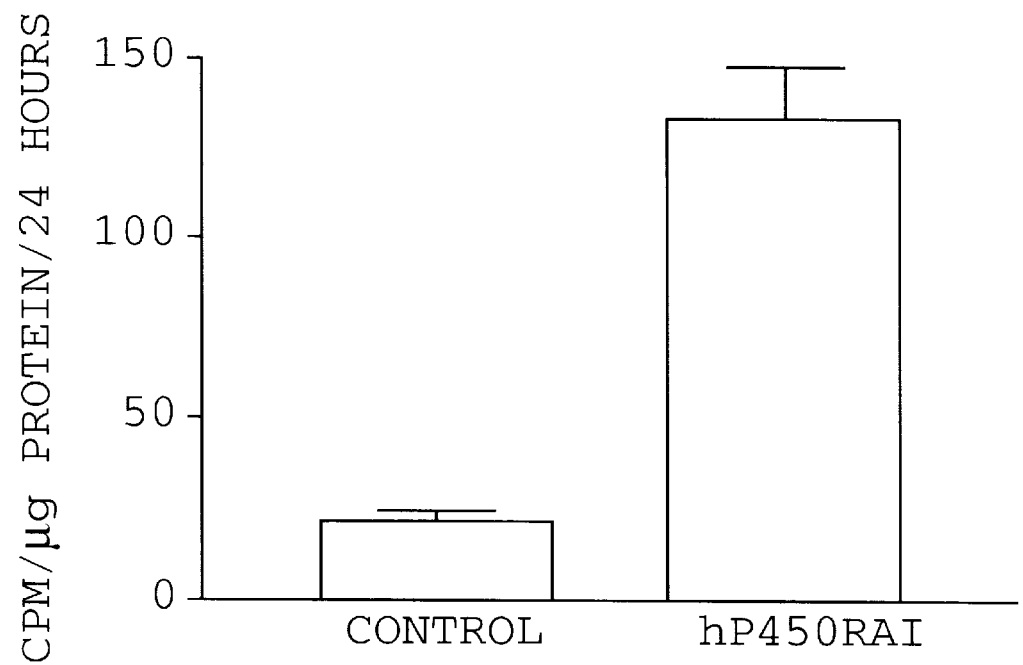
FIG. 11(a) shows 4-oxo-RA production of pSG5-hP450RAI transfected COS-1 cells and pSG5 transfected control cells.
Figure 11B:
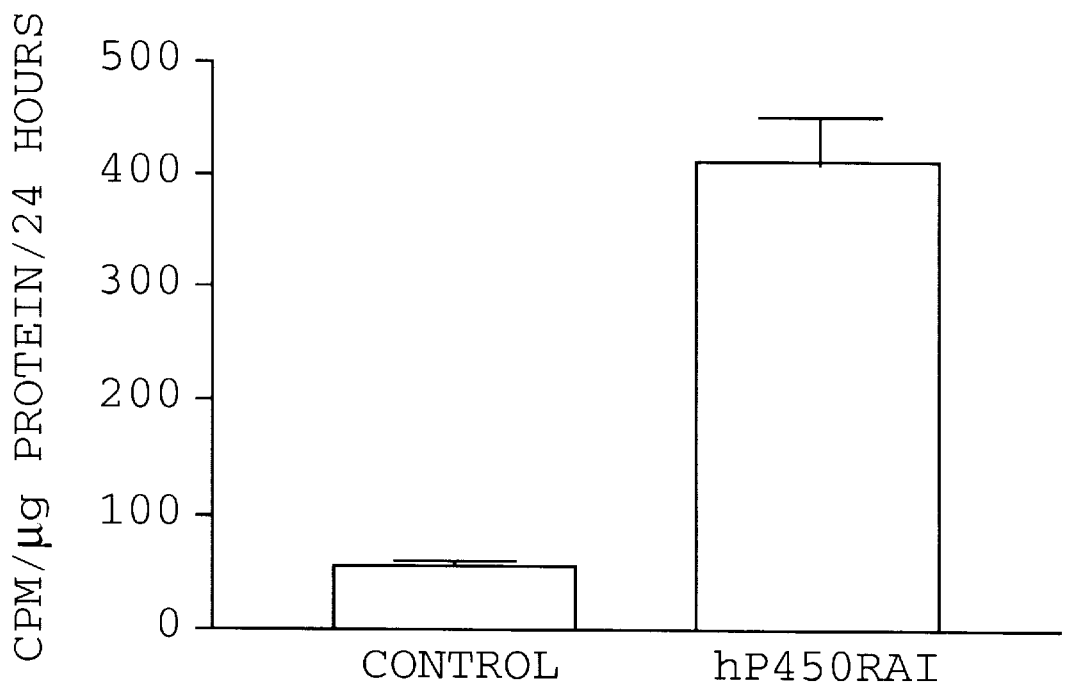
FIG. 11(b) shows 4-OH-RA production of pSG5-hP450RAI transfected COS-1 cells and pSG5 transfected control cells.
Figure 11C:
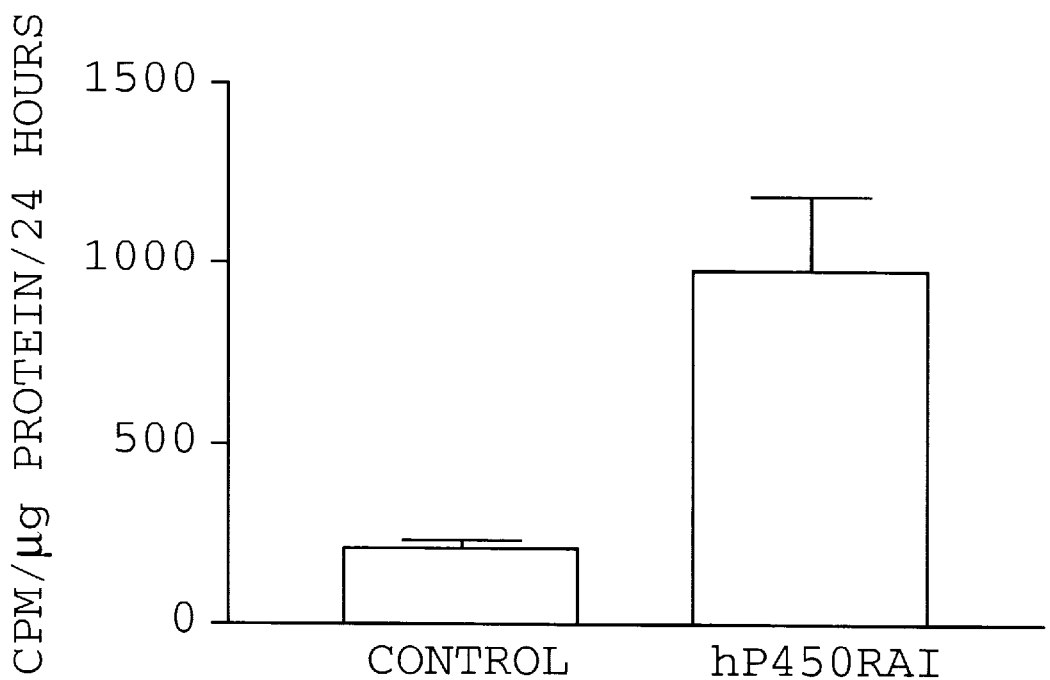
FIG. 11(c) shows formation of aqueous soluble metabolites of pSG5-hP450RAI transfected COS-1 cells and pSG5 transfected control cells.
Figure 11D:
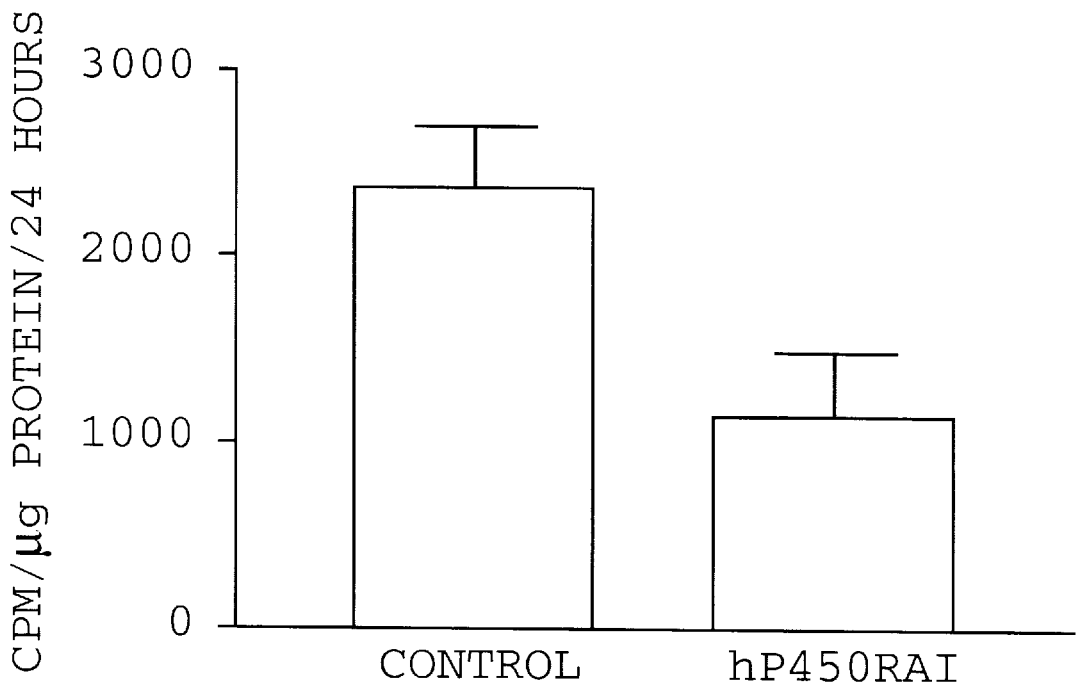
FIG. 11(d) shows unmetabolized RA of pSG5-hP450RAI transfected COS-1 cells and pSG5 transfected control cells.

COS-1 cells were subcultured 20 hours prior to transfection which was carried out according to the standard DEAE-dextran method [Sambrook, 1989 Maniatis, 1982]. Cells were transfected with pE-AR (adrenodoxin expression vector, 1 $\mu$g/P100 plate) and pE-ADX (adrenodoxin reductase expression vector, 1 $\mu$g/P100 plate) together with 3 $\mu$g per plate of either pSG5 (control) or hP450RAI-pSG5 (experimental). [11,12-$^3$H]all-trans retinoic acid (60,000 cpm per plate) was added 24 hours after transfection. Analyses were carried out as described in Example 3 and results obtained are shown in FIGS. 10 and 11(*a*) to 11(*d*). As indicated in the Figures, hP450RAI expression in COS-1 cells promoted conversion of RA into 4-OH-RA and 4-oxo-RA. Total amounts of 4-oxo-RA and 4-OH-RA produced in the transfected cells in comparison to amounts produced in the control cells are shown in FIGS. 11(*a*) and (*b*), respectively. Overall, greater amounts of aqueous soluble metabolites were produced in the transfected cells (FIG. 11 (*c*)) and greater amounts of unmetabolized RA were found in control cells (FIG. 11 (*d*)).

Figure 5:
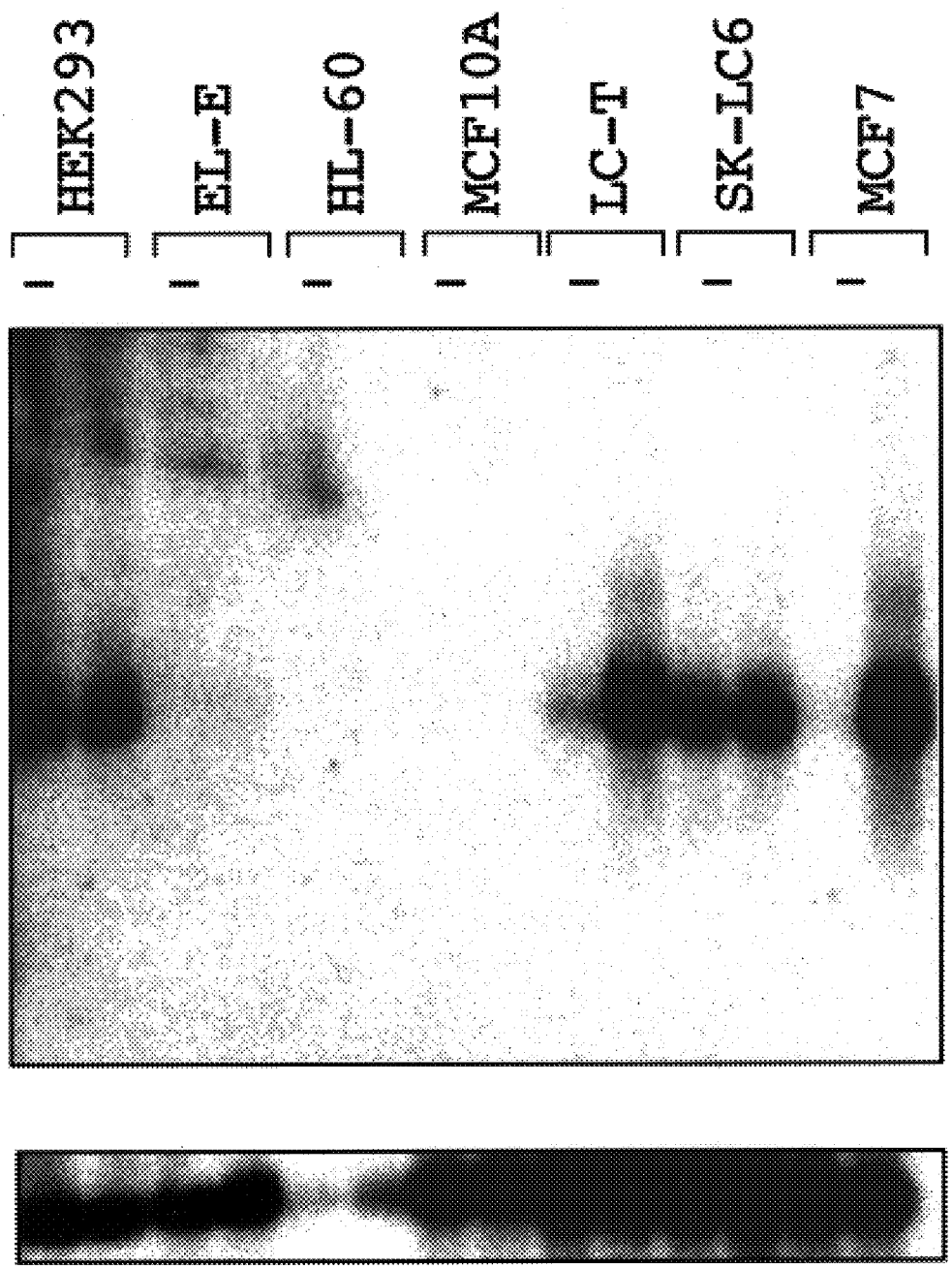
FIG. 5 shows results obtained with human cell lines probed with a α-[$^{32}$P]-dATP labeled probe having the sequence identified as SEQ ID NO:11: HEK293; EL-E; HL-60; MCF10A; LC-T; SK-LC6; and MCF7. (+) indicates pretreatment with $10^{-6}$M RA and (-) indicates no RA pretreatment. The blot was also probed with hGAPDH to control for RNA loading of the gel, shown in the bottom panel.
Figure 6:
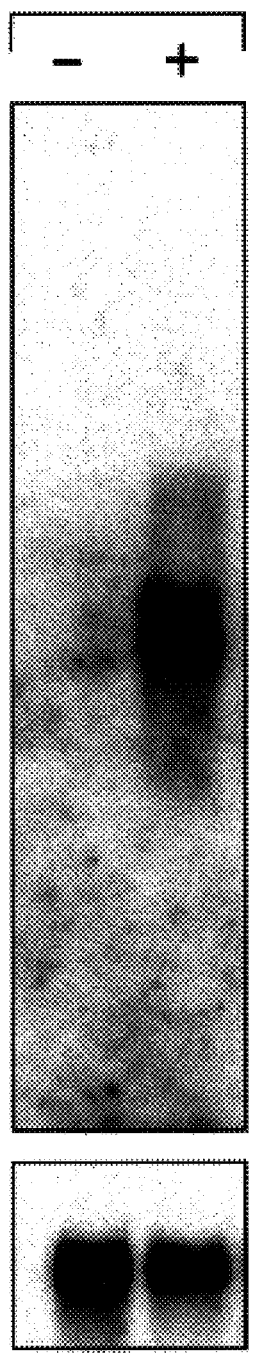
FIG. 6 is similar to FIG. 5 for the cell lines U937 and HepG2.
Figure 7:
FIG. 7 is similar to FIG. 5 for the NT2 cell line.

The clone sequence (SEQ ID NO:11) was prepared as a $^{32}$[P]-dATP labeled probe to study the inducibility of hP450RAI by RA in several cell lines: HEK293; EL-E; HL-60; MCF10A; LC-T; SK-LC6; MCF7; U937; HepG2; NT2 (See FIGS. 5 to 7). As can be seen, a variety of expression patterns were observed. The SK-LC6 human lung (epithelial) line appeared to constitutively express corresponding mRNA. There was apparently some increase in expression in the HEK293 (human embryonic kidney), LC-T (human lung epithelial), HepG2 (human liver, epithelial in morphology), NT2 (pluripotent human embryonic carcinoma) and U937 (human monomyelocytes) cell lines in response to addition of RA. There was a large dependence on exposure to RA in the MCF7 (human breast carcinoma (epithelial)) cell line. Some cell lines showed no expression in the absence or presence of RA: EL-E; HL-60 and MCF10A.

Figure 8:
FIG. 8 is similar to FIG. 5 for a normal NB4 cell line (first two lanes) and three individually derived retinoic acid resistant NB4 derivative cell lines.

The $^{32}$[P]-dATP labeled probe was also used to study hP450RAI mRNA expression in a human acute promyelocytic leukemia cell line. Experiments were carried out using the NB4 cell line, isolated from a human acute promyelocytic leukemia patient, and three retinoic acid resistant cell lines were independently derived from NB4. Results are shown in FIG. 8. As can be seen, the normal cells expressed hP450RAI mRNA after treatment with $10^{-6}$M RA, while such expression appeared to be absent for the other cell lines both in the absence and presence of RA.

Figure 12A:
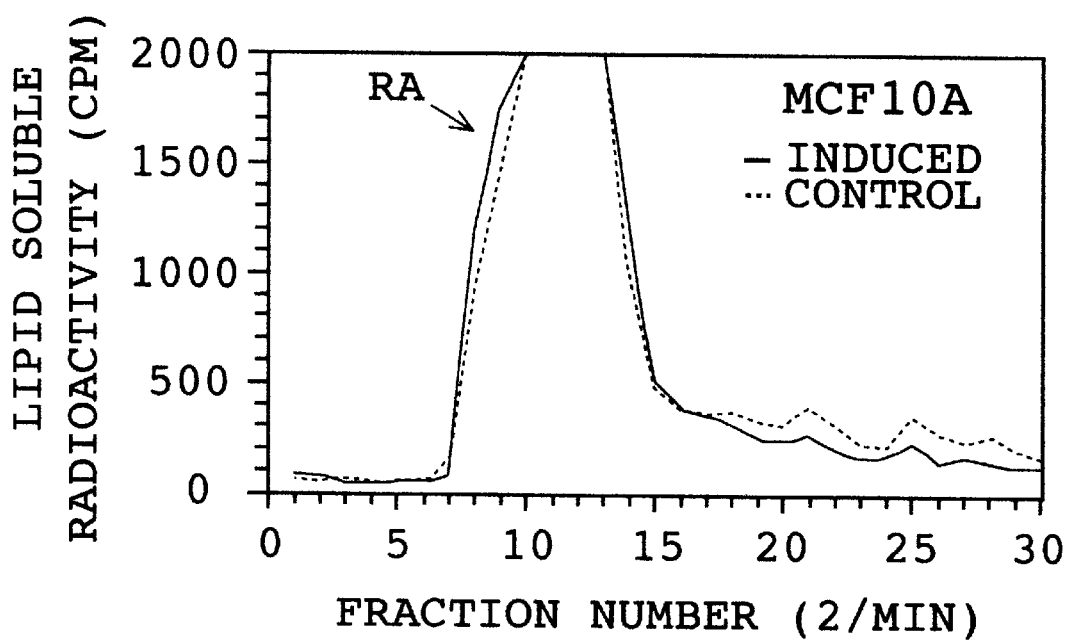
FIG. 12(a) shows elution profiles of lipid soluble extracts obtained from media of MCF10A cells exposed to RA and unexposed MCF10A control cells. Plots of cpm vs fraction number for cells incubated with [11,12-$^3$H]RA for 24 hours of RA-induced MCF10A cells (---) and control (———) are shown.
Figure 12B:
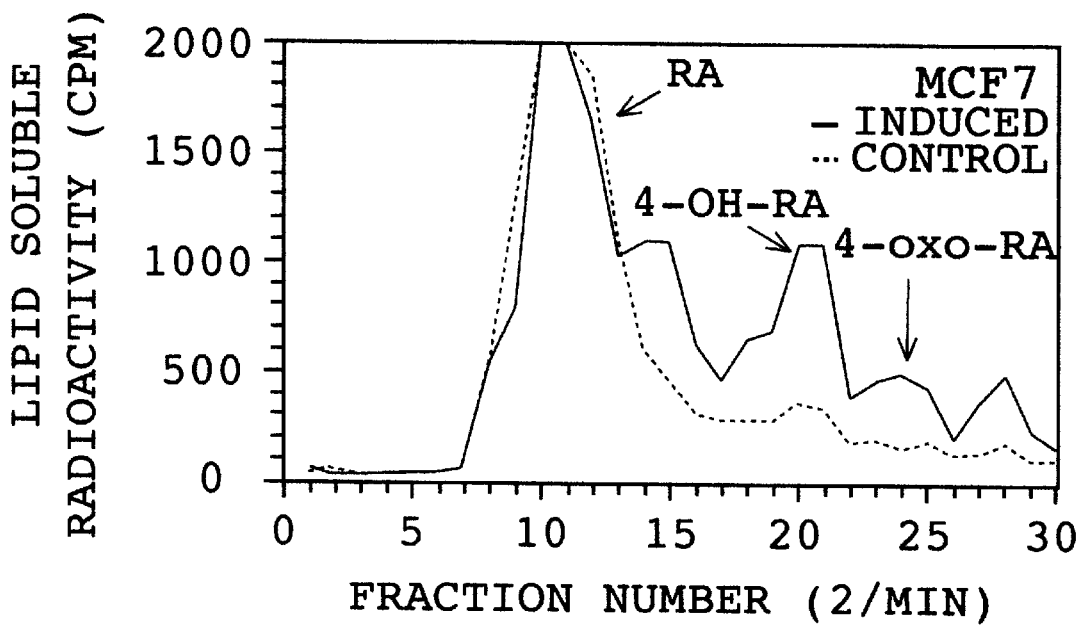
FIG. 12(b) shows elution profiles of lipid soluble extracts obtained from treated media of MCF7 cells exposed to RA and unexposed MCF7 control cells. Plots of cpm vs fraction number for cells incubated with [11,12-$^3$H]RA for 24 hours of RA-induced MCF7 cells (---) and control (———) are shown.
Figure 12C:
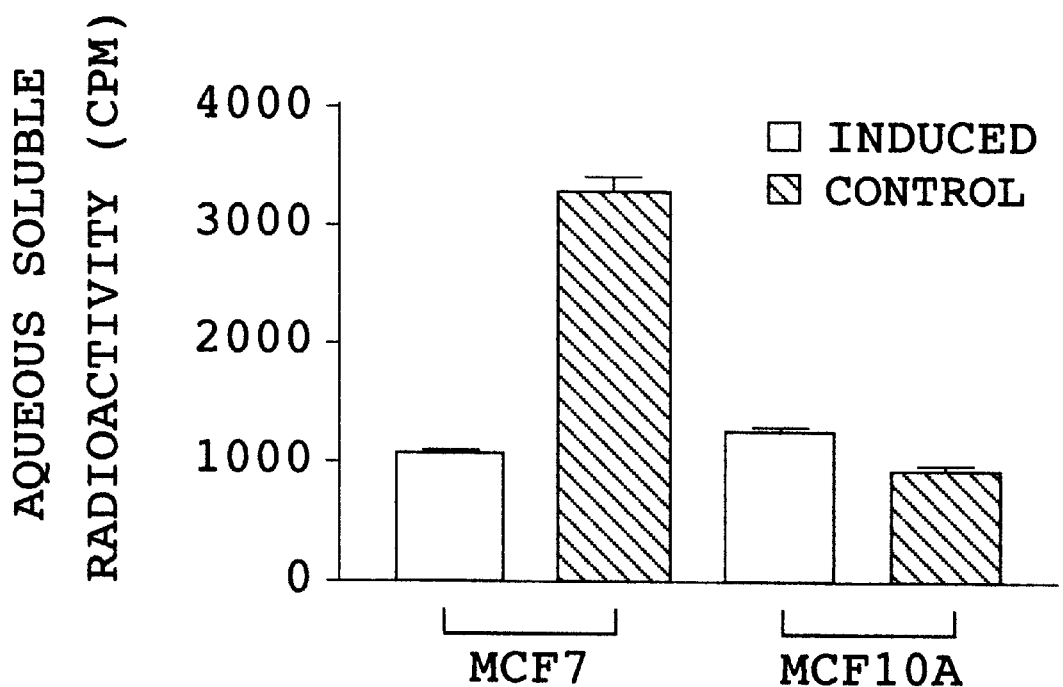
FIG. 12(c) shows the total aqueous soluble metabolites measured using aliquots of the aqueous soluble extract of the cell lines described in FIGS. 12(a) and (b) subjected to β-scintillation counting. The first two bars are for unexposed MCF7 cells and MCF7 cells exposed to RA, respectively. The third and fourth bars are for unexposed MCF10A cells and MCF10A cells exposed to RA, respectively.

Analysis of metabolites of MCF10A and MCF7 cell lines exposed to RA was carried out, MCF10A cells having displayed no expression of mRNA and latter having displayed a large dependence of mRNA expression on exposure to RA. The results are shown in FIGS. 12(a) to 12(c). Consistent with the results shown in FIG. 5, the results shown in FIG. 12(a) indicate there was little difference in the lipid soluble activity profiles of the MCF10A cell line exposed to RA and the control. The last two bars of FIG. 12 (c) indicate that total aqueous soluble metabolites were about the same for both the induced and control MCF10A cells. As indicated in FIG. 12(b), the MCF7 cell line exposed to RA had an elution profile which indicated significantly greater concentrations of 4-OH-RA and 4-oxo-RA than the same cell line not exposed to RA. FIG. 12(c) indicates that the amount of total aqueous soluble metabolites of the MCF7 cells exposed to RA was much greater than that for the control cells. Again, these results are consistent with those obtained in the blotting results shown in FIG. 5 for the MCF7 cell line.

A 1.3 kb cDNA of hP450RAI was mapped using a P-1 derived artificial chromosome (PAC) library. Mapping of the cDNA and genomic PAC clone was performed by fluorescence in situ hybridization [Lichter, 1990] to normal human lymphocyte chromosomes counterstained with propidium iodide and DAPI. Biotinylated probe was detected with avidin-fluorescein isothiocyanate (FITC). Images of metaphse preparations were captured by a thermoelectrically cooled charge coupled camera (Photometrics, Tucson, Ariz.). Separate images of DAPI banded chromosomes [Heng, 1993] and FITC targeted chromosomes were obtained. Hybridization signals were aequired and merged using image analysis software and pseudo colored blue (DAPI) and yellow (FTIC) [Boyle, 1992] and overlaid electronically.

Positive hybridization signals were found to be localized to 10q23–24. The band assignment was determined by measuring the fractional chromosome length and by analyzing the banding pattern generated by the DAPI counterstained image.

Genomic sequences can thus be sequenced. Oligonucleotides for use as primers are synthesized according to the DNA sequence of hP450RAI. These are then used to generate further primers corresponding to genomic DNA flanking hP450RAI and the complete sequence of the genomic locus determined.

It is possible to compare the zP450RAI and hP450RAI sequences described above. Of the 492 amino acids of zP450RAI (SEQ ID NO:2), it is possible to align 334 amino acids with the 497 amino acids of hP450RAI (SEQ ID NO:4). See FIG. 9. On this basis, there is about 68% homology between the human and fish proteins. The degree of homology between the two amino acid sequences is slightly greater towards the C-terminus than in the N-terminus region. It also appears as though nucleic acid sequences encoding the conserved sequence Met-Lys-Arg-Gln-Lys (amino acid numbers 70 to 74 of zP450RAI) can be used as a probe to obtain corresponding proteins from cDNA libraries of other species.

It has also been found by the present inventors (results not shown) that RA can induce mRNA transcripts which cross hybridize with a P450RAI cDNA probe in either of the F9 and P19 mouse cell lines having 4-hydroxylase activity, as described by Blumberg et al. [Blumberg et al., 1995; Achkar et al., 1996].

As mentioned above, RA-induced expression of a protein by the cells described herein involves a regulatory sequence which is located upstream of the coding sequence of DNA that it controls. In the case of preferred embodiments described so far, the protein has been P450RAI, whether in cells of the zebrafish, human or other organism. Such a cell can be modified by incorporating DNA encoding a different protein into the region of the gene which encodes P450RAI. An approach very likely to succeed involves excision of the P450RAI DNA and replacement thereof with the different coding sequence. In this way, a cellular system for producing proteins that is inducible by exposure to a retinoid, preferably RA, is obtained. It may be that the regulatory sequence is directly responsive to the presence of RA, causing mRNA to be produced de novo with subsequent translation thereof into the protein. In such case it is possible to incorporate the regulatory DNA sequence operably linked to a protein-encoding sequence into a conventional genetically engineered protein-producing cell and induce the production of the desired protein by exposure of the cell to RA.

RNA antisense sequences (nucleic acids or oligonucleotides) that inhibit cellular RA-induced P450RAI production can be used to inhibit metabolism of RA by P450RAI [Monia, 1996]. Antisense oligonucleotides, typically 15 to 20 bases long, bind to the sense mRNA or pre mRNA region coding for the protein of interest, which can inhibit translation of the bound mRNA to protein. The cDNA sequence encoding hP450RAI can thus be used to design a series of oligonucleotides which together cover the a large portion, or even the entire cDNA sequence. These oligonucleotides can be tested to determine which provides the greatest inhibitory effect on the expression of the protein. This can be done by exposing cells to the various oligonucletides and measuring subsequent changes in hP450 activity. The most suitable mRNA target sites include 5'- and 3'-untranslated regions as well as the initiation codon. Other regions might be found to be more or less effective.

More directly, use of suitable antibodies that bind to the P450RAI protein so as to inhibit binding of RA would reduce RA metabolism by P450RAI. Other approaches involving inhibition of P450RAI action by might be more preferable.

The present invention thus includes a method of screening drugs for their effect on activity of a retinoic acid inducible protein. The method includes exposing the protein to a prospective inhibitor drug and determining the effect on protein activity. The measured activity might be hydroxylation of a retinoid, particularly all-trans retinoic acid, or hydroxylation of a retinoic acid, particularly all-trans retinoic acid, at the 4 position of the β-ionone ring thereof. For screening drugs for use in humans, hP450RAI itself is particularly useful for testing the effectiveness of such drugs.

Prospective drugs could also be tested for inhibition of the activity of other P450 cytochromes, which are desired not to be inhibited. In this way, drugs which selectively inhibit hP450RAI over other P450s could be identified.

Another system for screening for potential inhibitors of a P450RAI protein includes a stably transfected cell line having incorporated therein DNA of a reporter gene (e.g., β-galactosidase, firefly luciferase, or the like) and of the P450RAI, in which expression of both genes is inducible by exposure of the cells to RA. Expression of the reporter gene provides a measure of the inducement of the expression system and therefore provides an indication of the amount of RA present. Exposure of the cells to RA leads to RA metabolism and, with time, such metabolism leads to a decrease in the degree of inducement which is indicated by the reporter protein. Exposure of the cells to RA in the presence of an agent that inhibits P450RAI metabolism of RA results in decreased RA metabolism, whereas exposure of the cells to RA in the presence of an agent that does not inhibit P450RAI metabolism of RA has no effect on RA metabolism. A comparison of expression of the reporter gene in the presence of RA alone and in the presence of both RA and a potential inhibitory drug thus gives a measure of the effectiveness of the drug in inhibiting metabolism of RA by the P4540RAI protein.

There is the possibility that cellular retinoic acid-binding protein (CRABP) [Adamson, 1993] is involved in binding of a retinoid substrate to a P450RAI protein of the present invention. The effect of the presence of CRABP, derivatives, synthetic fragments or analogs thereof could thus be determined according to screening methods of the present invention; effectiveness of such agents in enhancing RA metabolism can also be determined.

It will of course be understood, without the intention of being limited thereby, that a variety of substitutions of amino acids is possible while preserving the structure responsible for retinoid metabolizing acitivity of the proteins disclosed herein. Conservative substitutions are described in the patent literature, as for example, in U.S. Pat. No. 5,2264,558. It is thus expected, for example, that interchange among non-polar aliphatic neutral amino acids, glycine, alanine, proline, valine and isoleucine, would be possible. Likewise, substitutions among the polar aliphatic neutral amino acids, serine, threonine, methionine, asparagine and glutamine could possibly be made. Substitutions among the charged acidic amino acids, aspartic acid and glutamic acid, could probably be made, as could substitutions among the charged basic amino acids, lysine and arginine. Substitutions among the aromatic amino acids, including phenylalanine, histidine, tryptophan and tyrosine would also likely be possible. These sorts of substitutions and interchanges are well known to those skilled in the art. Other substitutions might well be possible. Of course, it would also be expected that the greater the percentage of homology of a variant protein with a naturally occuring protein, the greater the retention of metabolic activity.

Also, an antibody can be linked to or conjugated with a reporter system which is set up to indicate positively binding of the protein to the antibody. Well known reporter systems include radioimmuno assays (RIAs) or immunoradiometric assays (IRMAs). Alternatively, an enzyme-linked immunosorbent assay (ELISA) would have in common with RIAs and IRMAs a relatively high degree of sensitivity, but would generally not rely upon the use of radioisotopes. A visually detectable substance may be produced or at least one detectable in a spectrophotometer. An assay relying upon fluroescence of a substance bound by the enzyme being assayed could be used. It will be appreciated that there are a number of reporter systems which may be used, according to the present invention, to detect the presence of a particular protein. With standardized sample collection and treatment, protein presence above a threshold amount in blood serum could well be determined.

Such an antibody-linked reporter system could be used in a method for determining whether a fluid sample of a subject contains a deficient amount or an excessive amount of the protein. Given a normal threshold concentration of such a protein for a given type of subject, test kits could thus be developed.

A further advantage may be obtained through chimeric forms of the protein, as known in the art. A DNA sequence encoding the entire protein, or a portion of the protein, could thus be linked with a sequence coding for the C-terminal portion of E. coli β-galactosidase to produce a fusion protein, for example. An expression system for human respiratory syncytial virus glycoproteins F and G is described in U.S. Pat. No. 5,288,630 issued Feb. 22, 1994 and references cited therein, for example.

References

Particulars of references cited above are given below. All of the listed references are incorporated herein by reference.

Adamson, P. C., Boylan, J. F., Balis, F. M., Murphy, R. F., Godwin, K. A., Gudas, L. J. and Poplack, D. G. (1993). Time course of induction of metabolism of all-trans retinoic acid and the up-regulation of cellular retinoic acid-binding protein. Cancer Research 56, 675–8.

Achkar, C. C., Derguini, F., Blumberg, B., Langston, A., Arthur, A. L., Speck, J., Evans, R. M., Bolado, Jr., J. Nakanishi, K. and Buck, J. (1996) 4-Oxoreinol, a new natural ligand and transactivator of the retinoic acid receptors. Proc. Natl. Acad. Sci. USA 93, 4879–84.

Akimenko, M. A. and Ekker, M. (1995a). Anterior duplication of the Sonic hedgehog expression pattern in the pectoral fin buds of zebrafish treated with retinoic acid. Developmental Biology 170, 243–7.

Akimenko, M. A., Johnson, S. L., Westerfield, M. and Ekker, M. (1995b). Differential induction of four msx homeobox genes during fin development and regeneration in zebrafish. Development 121, 347–57.

Akiyoshi-Shibata, M., Sakaki, T., Ohyama, Y., Noshiro, M., Okuda, K. and Yabusaki, Y. (1994). Further oxidation of hydroxycalcidiol by calcidiol 24-hydroxylase. A study with the mature enzyme expressed in Escherichia coli. European Journal of Biochemistry 224, 335–43.

Bligh, E. G. and Dyer, W. J. (1957). A rapid method of total lipid extraction and purification. Canadian Journal of Biochemistry 37, 911–917.

Blumberg, B., Bolado, Jr., J., Derguini, F., Craig, A. G., Moreno, T. A., Chakravarti, D., Heyman, R. A., Buck, J. and Evans, R. M. (1996) Novel retinoic acid receptor ligands in Xenopus embryos. Proc. Natl. Acad. Sci. USA 93, 4873–78.

Boylan, J. F., Lufkin, T., Achkar, C. C., Taneha, R., Chambon, P. and Gudas, L. J. (1995). Targeted Disruption of Retinoic Acid Receptor a (RARa) and RARg Results in Receptor-Specific Alterations in Retinoic Acid-Mediated Differentiation and Retinoic Acid Metabolism. Mol. Cell Biol. 15, 843–851.

Boyle, A. L. et al. (1992). Genomics 12, 106–15.

Chambon, P. (1995). The molecular and genetic dissection of the retinoid signaling pathway. [Review]. Recent Progress in Hormone Research 50, 317–32.

Chen, K. S. and DeLuca, H. F. (1995). Cloning of the human 1 alpha,25-dihydroxyvitamin D-3 24-hydroxylase gene promoter and identification of two vitamin D-responsive elements. Biochimica et Biophysica Acta 1263, 1–9.

Costaridis, P., Horton, C., Zeitlinger, J., Holder, N. and Maden, M. (1996). Endogenous Retinoids in the Zebrafish Embryo and Adult. Developmental Dynamics 205, 41–51.

Creech Kraft, J., Schuh, T., Juchau, M. R. and Kimelman, D. (1994). Temporal distribution, localization and metabolism of all-trans retinol, didehydroretinol and all-trans retinal during Xenopus development. Biochem. J. 301, 111–119.

Duell, E. A., Astrom, A., Griffiths, C. E., Chambon, P. and Voorhees, J. J. (1992). Human skin levels of retinoic acid and cytochrome p-450-derived 4-hydroxyretinoic acid after topical application of retinoic acid in vivo compared to concentrations required to stimulate retinoic acid receptor-mediated transcription in vitro. Journal of Clinical Investigation 90, 1269–74.

Duell, E. A., Astrom, A., Kang, S., Griffiths, C. E. M. and Voorhees, J. (1994). All-trans, 9-cis and 13-cis retinoic acid each induce a cytochrome P450 4-retinoic acid hydroxylase which causes all-trans but not 9-cis or 13-cis retinoic acid to self-metabolize. Society for Investigative Dermatology Abstracts 102, 641.

Fiorella, P. D., Giguere, V. and Napoli, J. L. (1993). Expression of Cellular Retinoic Acid-binding Protein (Type II) in Escherichia coli. The Journal of Biological Chemistry 268, 21545–21552.

Frolik, C. A., Roberts, A. B., Tavela, T. E., Roller, P. P., Newton, D. L. and Sporn, M. B. (1979). Isolation and identification of 4-hydroxy- and 4-oxoretinoic acid. In vitro metabolites of all-trans retinoic acid in hamster trachea and liver. Biochemistry 18, 2092–7.

Gotoh, O. and Fujii-Kuriyama, Y. (1989). Evolution, structure, and gene regulation of cytochrome P-450.

Green, S., Issemann, I. and Sheer, E. (1988). A versatile in vivo and in vitro eukaryotic expression vector for protein engineering. Nucleic Acids Research 16, 369–370.

Heng, H. and Tsui, L-C. (1993). Chromosome 102, 325–32.

Hozumi, N and Sandhu, J. S. (1993). Recombinant antibody technology, its advent and advances. Cancer Invest. 11, 714–723.

Jones, B. B., Ohno, C. K., Allenby, G., Boffa, M., Levin, A. A., Grippo, J. F. and Petkovich, M. (1995). New Retinoid X Receptor Subtypes in Zebra Fish (*Danio rerio*) Differentially Modulate Transcription and Do Not Bind 9-cis Retinoic Acid. Mol. Cell Biol. 15, 5226–5234.

Lammer, E. J., Chen, D. T., Hoar, R. M., Agnish, N. D., Benke, P. J., Braun, J. T., Curry, C. J., Fernhoff, P. M., Grix, A. J., Lott, I. T. et al. (1985). Retinoic acid embryopathy. New England Journal of Medicine 313, 837–41.

Lee, M. O., Dockham, P. and Sladek, N. (1990). Identification of human liver aldehyde dehydrogenases that catalyze the oxidation of retinaldehyde to retinoic acid. FASEB Journal 32, 156.

Liang, P. and Pardee, A. B. (1992). Differential display of eukaryotic messenger RNA by means of the polymerase chain reaction. Science 257, 967–71.

Lichter, P. et al. (1990). High Resolution Mapping of Chromosome 11 by in situ hybridization by cosmid clones. Science 247, 64–9.

Maden, M. and Holder, N. (1992). Retinoic acid and development of the central nervous system. [Review]. Bioessays 14, 431–8.

Makin, G., Lohnes, D., Byford, V., Ray, R. and Jones, G. (1989). Target cell metabolism of 1,25-dihydroxyvitamin D3 to calcitroic acid. Evidence for a pathway in kidney and bone involving 24-oxidation. Biochemical Journal 262, 173–80.

Maniatis et al. (1982) Molecular Cloning: A Laboratory Manual, Cold Spring Harbor.

Mangelsdorf, D. J. and Evans, R. M. (1995). The RXR Heterodimers and Orphan Receptors. Cell 83, 841–850.

Monia, B. P., Johnston, J. F., Geiger, T., Muller, M. and Fabbro, D. (1996). Antitumor activity of a phosphorothioate antisense oligodeoxynucleotide targeted against C-raf kinase. Nature Medicine 2, 668–75.

Morriss-Kay, G. (1993). Retinoic acid and craniofacial development: molecules and morphogenesis. [Review]. Bioessays 15, 9–15.

Muindi, J. R. F., Frankel, S. R., Huselton, C., DeGrazia, F., Garland, W., Young, C. W. and Warrell, R. P., Jr. (1992). Clinical pharmacology of oral all-trans retinoic acid in patients with acute promyelocytic leukemia. Cancer Research 52, 2138–2142.

Muindi, J. R., Young, C. W. and Warrell, R. J. (1994). Clinical pharmacology of all-trans retinoic acid. Leukemia 8, 1807–1812.

Nelson, D. R., Kamataki, T., Waxman, D. J., Guengerich, F. P., Estabrook, R. W., Feyereisen, R., Gonzalez, F. J., Coon, M. J., Gunsalus, I. C., Gotoh, O., Okuda, K. and Nebert, D. W. (1993). The P450 superfamily: update on new sequences, gene mapping, accession numbers, early trivial names of enzymes, and nomenclature. DNA & Cell Biology 12, 1–51.

Ohyama, Y., Ozono, K., Uchida, M., Shinki, T., Kato, S., Suda, T., Yamamoto, O., Noshiro, M. and Kato, Y. (1994). Identification of a vitamin D-responsive element in the 5'-flanking region of the rat 25-hydroxyvitamin D3 24-hydroxylase gene. Journal of Biological Chemistry 269, 10545–50.

Pijnappel, W. W., Hendriks, H. F., Folkers, G. E., van, den, Brink, Ce, Dekker, E. J., Edelenbosch, C., van, der, Saag, Pt and Durston, A. J. (1993). The retinoid ligand 4-oxoretinoic acid is a highly active modulator of positional specification. Nature 366, 340–4.

Reddy, A. P., Chen, J., Zacharewski, T., Gronemeyer, H., Voorhees, J. J. and Fisher, G. J. (1992). Characterization and purification of human retinoic acid receptor-g1 over-expressed in the baculovirus-insect cell system. Biochem. J. 287, 833–840.

Roberts, A. B., Nichols, M. D., Newton, D. L. and Sporn, M. B. (1979a). In vitro metabolism of retinoic acid in hamster intestine and liver. Journal of Biological Chemistry 254, 6296–302.

Roberts, A. B., Frolik, C. A., Nichols, M. D. and Sporn, M. B. (1979b). Retinoid-dependent induction of the in vivo and in vitro metabolism of retinoic acid in tissues of the vitamin A-deficient hamster. Journal of Biological Chemistry 254, 6303–9.

Sambrook, J., Fritsch E. F. and Maniatis, T. (1989). Molecular Cloning: A Laboratory Manual. Cold Spring Harbor Lab Press, Cold Spring Harbor, N.Y.

Takatsuka, J., Takahashi, N. and De Luca, L. M. (1996). Retinoic Acid Metabolism and Inhibition of Cell Proliferation: An Unexpected Liaison. Cancer Research 56, 675–678.

Thaller, C. and Eichele, G. (1990). Isolation of 3,4-didehydroretinoic acid, a novel morphogenetic signal in the chick wing bud. Nature 345, 815–9.

Van Wauwe, J. P., Coene, M.-C., Goossens, J., Van Nijen, G., Cools, W. and Lauwers, W. (1988). Ketoconazole inhibits the in vitro and in vivo metabolism of all-trans retinoic acid. The Journal of Pharmacology and Experimental Therapeutics 245, 718–722.

Van Wauwe, J. P., Coene, M.-C., Goossens, J., Cools, W. and Monbaliu, J. (1990). Effects of cytochrome P450 inhibitors on the in vivo metabolism of all-trans-retinoic acid in rats. The Journal of Pharmacology and Experimental Therapeutics 252, 365–369.

Van Wauwe, J., Van Nyen, G., Coene, M., Stoppie, P., Cools, W., Goossens, J., Borghgraef, P. and Janssen, P. A. J. (1992). Liarozole, an Inhibitor of Retinoic Acid Metabolism, Exerts Retinoid-Mimetic Effects in Vivo. The Journal of Pharmacology and Experimental Therapeutics 261, 773–779.

White, J. A., Boffa, M. B., Jones, B. and Petkovich, M. (1994). A zebrafish retinoic acid receptor expressed in the regenerating caudal fin. Development 120, 1861–72.

Williams, J. B. and Napoli, J. L. (1987). Inhibition of retinoic acid metabolism by imidazole antimycotics in F9 embryonal carcinoma cells. Biochemical Pharmacology 36, 1386–1388.

Windhorst, D. B. (1982). The use of isotretinoin in disorders of keratinization. Journal of the American Academy of Dermatology 6, 708–9.

Wouters, W., van, D. J., Dillen, A., Coene, M. C., Cools, W. and De, C. R. (1992). Effects of liarozole, a new antitumoral compound, on retinoic acid-induced inhibition of cell growth and on retinoic acid metabolism in MCF-7 human breast cancer cells. Cancer Research 52, 2841–6.

Zierold, C., Darwish, H. M. and DeLuca, H. F. (1995). Two vitamin D response elements function in the rat 1,25-dihydroxyvitamin D 24-hydroxylase promoter. Journal of Biological Chemistry 270, 1675–8.

What is claimed is:

1. An isolated nucleic acid molecule comprising a nucleotide sequence that hybridizes under high stringency conditions, wherein high stringency conditions include a wash step of about 0.2× SSC at 50° C., to the nucleotide sequence shown as SEQ ID NO:3 or SEQ ID NO:5, and encodes a protein that oxidizes a retinoid.

2. An isolated nucleic acid molecule comprising a nucleotide sequence that hybridizes under high stringency conditions, wherein high stringency conditions include a wash step of about 0.2× SSC at 50° C., to the nucleotide sequence shown as SEQ ID NO:3 or SEQ ID NO:5, and encodes a protein that hydroxylates retinoic acid at the 4 position of the β-ionone ring.

3. An isolated nucleic acid molecule comprising a nucleotide sequence identified as SEQ ID NO:3 or SEQ ID NO:5, or which varies from SEQ ID NO:3 or SEQ ID NO:5 in a coding region due to the degeneracy of the genetic code.

4. Isolated mRNA transcribed from DNA comprising a nucleic acid molecule of claim 3, wherein the mRNA is the full length of said nucleotide sequence.

5. Isolated DNA comprising a nucleic acid molecule of claim 3 in a recombinant cloning vector.

6. A said nucleic acid molecule of claim 1 wherein the sequence of the nucleic acid molecule comprises a part of a human genome or of a fish genome, or varies therefrom due to the degeneracy of the genetic code.

7. A said nucleic acid molecule of claim 2 wherein the sequence of the nucleic acid molecule comprises a part of a human genome or of a fish genome, or varies therefrom due to the degeneracy of the genetic code.

8. An isolated nucleic acid molecule encoding a protein comprising an amino acid sequence selected from the group consisting of SEQ ID NO:2 and SEQ ID NO:4.

9. The nucleic acid molecule of claim 1, wherein the retinoid is a retinol or a retinoic acid.

10. The nucleic acid of claim 1, wherein the protein oxidizes the carbon at the 4-position of the β-ionone ring of the retinoid.

11. The nucleic acid of claim 1, wherein the retinoid is an all-trans retinoid.

12. The nucleic acid of claim 2, wherein the retinoic acid is all-trans.

13. An isolated nucleic acid molecule which is antisense to the full length of a nucleic acid molecule as claimed in claim 1.

14. An isolated nucleic acid molecule which is antisense to the full length of a nucleic acid molecule as claimed in claim 2.

15. An isolated nucleic acid molecule which is antisense to a nucleic acid molecule comprising a nucleotide sequence shown as SEQ ID NO:3 or SEQ ID NO:5.

16. An isolated nucleic acid molecule that hybridizes under high stringency conditions, wherein high stringency conditions include a wash step of about 0.2× SSC at 50° C., to 5' untranslated region of the nucleotide sequence shown in SEQ ID NO:3.

17. A recombinant expression vector suitable for transformation of a host cell comprising a nucleic acid molecule as claimed in claim 1 and at least one regulatory sequence operatively linked to the nucleic acid molecule.

18. The recombinant expression vector of claim 17, wherein the nucleic acid molecule is operatively linked to said at least one regulatory sequence to allow expression of said protein.

19. The recombinant expression vector of claim 17, wherein the nucleic acid molecule is operatively linked to said at least one regulatory sequence to allow expression of an RNA molecule which is antisense to the nucleic acid molecule.

20. A transformant cell including a recombinant expression vector as claimed in claim 18.

21. A transformant host cell including a recombinant expression vector as claimed in claim 19.

22. The transformant host cell of claim 20 which is a mammalian cell.

23. The transformant host cell of claim 21 which is a mammalian cell.

24. A microbial cell containing and expressing heterologous human or zebrafish DNA encoding a retinoic acid inducible cytochrome P450 which oxidizes a retinoic acid or a retinol at the 4 position and/or the 18 position of the β-ionone ring.

25. The microbial cell of claim 24 wherein the retinoid which induces expression of the protein is retinoic acid.

26. The microbial cell of claim 24 wherein the heterologous DNA encodes a retinoid inducible protein having all-trans retinoic acid hydroxylase activity.

27. A microbial cell containing and expressing heterologous DNA which is complementary to the full coding region of a nucleic acid molecule of claim 1.

28. A stably transfected cell line which expresses a protein that oxidizes a retinoid, the cell line having incorporated transfected DNA encoding said protein that hybridizes under high stringency conditions, wherein high stringency conditions include a wash step of about 0.2× SSC at 50° C., to the nucleotide sequence shown as SEQ ID NO:3 or SEQ ID NO:5.

29. The cell line of claim 28 wherein production of the protein is inducible by exposing the cell line to retinoic acid.

30. The cell line of claim 29 which is a mammalian cell line.

31. A process for producing a retinoid metabolizing protein, comprising the steps of:

preparing a DNA fragment comprising a nucleotide sequence that hybridizes under high stringency conditions, wherein high stringency conditions include a wash step of about 0.2× SSC at 50° C., to the nucleotide sequence shown as SEQ ID NO:3 or SEQ ID NO:5, and encodes a protein that oxidizes a retinoid;

incorporating the DNA fragment into an expression vector to obtain a recombinant DNA molecule which comprises the DNA fragment and which undergoes replication in a cell;

transforming a host cell with the recombinant DNA molecule to produce a transformant cell which expresses said protein under pre-selected conditions;

culturing the transformant cell to produce said protein; and recovering said protein from resulting culture mixture.

32. A method for preparing a retinoid metabolizing protein comprising culturing a transformant host cell including a recombinant expression vector as claimed in claim 18 in a suitable medium until a retinoid metabolizing protein is formed and isolating the protein.

* * * * *

UNITED STATES PATENT AND TRADEMARK OFFICE
CERTIFICATE OF CORRECTION

PATENT NO.    : 6,063,606
DATED         : May 16, 2000
INVENTOR(S)   : P. Martin Petkovich et al.

It is certified that error appears in the above-identified patent and that said Letters Patent is hereby corrected as shown below:

Title page,
Item [73], insert:
-- [73] Assignee:    Queen's University at Kingston, Canada. --

Signed and Sealed this

Thirteenth Day of November, 2001

Attest:

*Nicholas P. Godici*

NICHOLAS P. GODICI
*Attesting Officer*    *Acting Director of the United States Patent and Trademark Office*